United States Patent [19]

Chandraratna

[11] Patent Number: 5,468,879

[45] Date of Patent: Nov. 21, 1995

[54] DISUBSTITUTED ACETYLENES BEARING HETEROBICYCLIC GROUPS AND HETEROAROMATIC OR PHENYL GROUPS HAVING RETINOID LIKE ACTIVITY

[75] Inventor: Roshantha A. S. Chandraratna, El Toro, Calif.

[73] Assignee: Allergan, Inc., Irvine, Calif.

[21] Appl. No.: 126,933

[22] Filed: Sep. 24, 1993

Related U.S. Application Data

[60] Division of Ser. No. 836,635, Feb. 14, 1992, Pat. No. 5,264,578, which is a continuation-in-part of Ser. No. 326,191, Mar. 20, 1989, Pat. No. 5,089,509, which is a continuation-in-part of Ser. No. 246,037, Sep. 19, 1988, abandoned, which is a continuation of Ser. No. 28,279, Mar. 20, 1987, abandoned.

[51] Int. Cl.$^6$ ............... C07D 335/04; C07D 311/04; C07D 311/76
[52] U.S. Cl. ............... 549/23; 549/398; 549/406
[58] Field of Search ................... 549/406, 398, 549/23

[56] References Cited

U.S. PATENT DOCUMENTS

| | | | |
|---|---|---|---|
| 4,096,341 | 6/1978 | Frazer | 560/85 |
| 4,326,055 | 4/1982 | Loeliger | 549/339 |
| 4,391,731 | 7/1983 | Boller et al. | 252/299.62 |
| 4,695,649 | 9/1987 | Magami et al. | 560/88 |
| 4,723,028 | 2/1988 | Shudo | 549/339 |
| 4,739,098 | 4/1988 | Chandraratna | 560/8 |
| 4,740,519 | 4/1988 | Shroot et al. | 514/443 |
| 4,810,804 | 3/1989 | Chandraratna | 549/23 |
| 4,826,969 | 5/1989 | Maignan et al. | 536/55.2 |
| 4,855,320 | 8/1989 | Chatterjee et al. | 549/313 |
| 4,895,868 | 1/1990 | Chandraratna | 549/23 |
| 4,980,369 | 12/1990 | Chandraratna | 549/23 |
| 4,992,468 | 2/1991 | Chandraratna | 514/532 |
| 5,006,550 | 4/1991 | Chandraratna | 549/407 |
| 5,013,744 | 5/1991 | Chandraratna | 549/339 |
| 5,015,658 | 5/1991 | Chandraratna | 549/23 |
| 5,023,341 | 6/1991 | Chandraratna | 549/23 |
| 5,037,825 | 8/1991 | Klaus et al. | 514/233.8 |
| 5,045,551 | 9/1991 | Chandraratna | 546/269 |
| 5,053,523 | 10/1991 | Chandraratna | 549/406 |
| 5,068,255 | 11/1991 | Chandraratna | 549/339 |
| 5,089,509 | 2/1992 | Chandraratna | 549/339 |
| 5,130,335 | 7/1992 | Chandraratna | 514/510 |
| 5,134,159 | 7/1992 | Chandraratna | 514/456 |
| 5,162,546 | 11/1992 | Chandraratna | 549/23 |
| 5,175,185 | 12/1992 | Chandraratna | 514/445 |
| 5,183,827 | 2/1993 | Chandraratna | 514/444 |
| 5,202,471 | 4/1993 | Chandraratna | 562/473 |
| 5,231,113 | 7/1993 | Chandraratna | 514/510 |
| 5,234,926 | 8/1993 | Chandraratna | 514/253 |
| 5,248,777 | 9/1993 | Chandraratna | 546/165 |
| 5,264,456 | 11/1993 | Chandraratna | 514/461 |
| 5,264,578 | 11/1993 | Chandraratna | 546/269 |

FOREIGN PATENT DOCUMENTS

| | | | |
|---|---|---|---|
| 0130795 | 1/1985 | European Pat. Off. | C07D 311/58 |
| 176034A | 4/1986 | European Pat. Off. | C07C 63/66 |
| 0272921 | 6/1988 | European Pat. Off. | C07D 213/80 |
| 0284288 | 9/1988 | European Pat. Off. | C07D 401/04 |
| 0350846 | 7/1989 | European Pat. Off. | C07D 311/58 |
| 3708060 | 9/1987 | Germany | C07D 311/04 |

OTHER PUBLICATIONS

A General Synthesis of Terminal and Internal Arylalkynes by the Palladium–Catalyzed Reaction of Alkynylzinc Reagents with Aryl Halides by Anthony O. King and Ei–ichi Negishi, *J. Org. Chem.*, 43, No. 2, 1978, p. 358.

Conversion by Methyl Ketones into Terminal Acetylenes and (E)–Tri–substituted Olefins of Terpenoid Origin by Ei–ichi, Anthony O. King, and William L. Klima, *J. Org. Chem.*, 45, No. 12, 1980, p. 2526.

Sporn et al. in *J. Amer. Acad. Derm.*, 15:756–764 (1986).

A Convenient Synthesis of Ethynylarenes and Diethynylarenes by S. Takahashi, Y. Kuroyama, K. Sonogashira, N. Hagihara, *Synthesis*, 1980, pp. 627–630.

Shudo et al. in *Chem. Phar. Bull.* 33:404–407 (1985).

Kagechika et al. in *J. Med. Chem.*, 31:2182–2192 (1988).

Chemistry and Biology of Synthetic Retinoids by Marcia I. Dawson and William H. Okamura, published by CRC Press Inc., 1990, pp. 334–335, 354.

Synthesis of 2,2'–Diacyl–1,1'–biaryls. Regiocontrolled Protection of . . . by Mervic, et al., *J. Org. Chem.*, No. 45, pp. 4720–4725, 1980.

(List continued on next page.)

*Primary Examiner*—C. Warren Ivy
*Assistant Examiner*—Raymond Covington
*Attorney, Agent, or Firm*—Gabor L. Szekeres; Robert J. Baran; Martin A. Voet

[57] ABSTRACT

Compounds of the formula

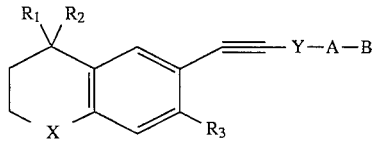

where $R_1$ and $R_2$, independently are alkyl groups having 2 to 8 carbons; $R_3$ is hydrogen or lower alkyl; X is S, O or N—$R_4$ where $R_4$ is hydrogen or lower alkyl; Y is phenyl or pyridyl, thienyl, furyl, pyridazinyl, pyrimidinyl, and pyrazinyl; A is $(CH_2)_n$ where n is 0–5, or lower branched chain alkyl, alkenyl having 2 to 6 carbons and 1 or 2 double bonds, alkynyl having 2 to 6 carbons and 1 or 2 triple bonds; B is hydrogen, COOH or a salt thereof, COOR$_5$, CONR$_6$R$_7$, —CH$_2$OH, CH$_2$OR$_8$, CH$_2$OCOR$_8$, CHO, CH(OR$_9$)$_2$, CHOR$_{10}$O, —COR$_{11}$, CR$_{11}$(OR$_9$)$_2$, or CR$_{11}$OR$_{10}$O, where $R_5$ is alkyl of 1 to 10 carbons, or cycloalkyl of 5 to 10 carbons, or $R_5$ is phenyl or lower alkylphenyl, $R_6$ and $R_7$ independently are hydrogen, alkyl of 1 to 10 carbons, or cycloalkyl of 5 to 10 carbons, or phenyl or lower alkylphenyl, $R_8$ is alkyl of 1 to 10 carbons, phenyl or lower alkylphenyl, $R_9$ is lower alkyl, $R_{10}$ is divalent alkyl radical of 2–5 carbons and $R_{11}$ is alkyl, cycloalkyl or alkenyl containing 1 to 5 carbons, have retinoic acid like activity.

20 Claims, No Drawings

OTHER PUBLICATIONS

A Dopamine Receptor Model and Its Application in the Design of a New Class of Rigid Pyrrolo[2,3–g]isoquinoline Antipsychotics, Gary L. Olson, et al. *American Chemical Society*, 1981, vol. 24, No. 9, pp. 1026–1031.

6.2.3 Conformational Restriction, Williams, et al., *Drug Discovery and Development*, 1987 The Human Press, pp. 54–55.

V. Retinoid Structure–Biological Activity Relationships, Chemistry and Biology of Synthetic Retinoids, pp. 324–356.

Davis et al., *J. Organomettalic Chem.* 387 (1990) 381–390.

Effects of 13–Cis–Retinoic Acid, All–Trans–Retinoic Acid, and Acitretin on the Proliferation, Lipid Synthesis and Keratin Expression of Cultured Human Sebocytes In Vitro, C. C. Zouboulis, *The Journal of Investigative Dermatology*, vol. 96, No. 5, May 1991, pp. 792–797.

Organ maintenance of human sebaceous glands: in vitro effects of 13–cis retinoic acid and testosterone, John Ridden, et al., *Journal of Cell Science*, vol. 95, 1990, pp. 125–136.

Characterization of Human Sebaceous Cells In Vitro, Thomas I. Doran, et al., *The Journal of Investigative Dermatology*, vol. 96, No. 3, Mar. 1991.

DISUBSTITUTED ACETYLENES BEARING HETEROBICYCLIC GROUPS AND HETEROAROMATIC OR PHENYL GROUPS HAVING RETINOID LIKE ACTIVITY

CROSS-REFERENCE TO RELATED APPLICATION

The present application is a divisional application Ser. No. 07/836,635, filed on Feb. 14, 1992, to be issued as U.S. Pat. No. 5,264,578, which is a continuation-in-part of application Ser. No. 07/326,191, filed on Mar. 20, 1989, expected to be issued as U.S. Pat. No. 5,089,509 on Feb. 18, 1992, which in turn was a continuation-in-part of application Ser. No. 07/246,037, filed on Sep. 15, 1988, now abandoned, which itself was a continuation of application Ser. No. 028,279, filed on Mar. 20, 1987, now abandoned.

BACKGROUND OF THE INVENTION

1. Field of the Invention

The present invention is directed to novel compounds which have retinoic acid-like biological activity. More specifically, the present invention relates to compounds having an ethynyl-heteroaromatic or an ethynyl-phenyl portion and a second portion which is an alkyl-substituted thiochromanyl, chromanyl or tetrahydroquinolinyl group. The present invention also relates to pharmaceutical compositions comprising these compounds and to methods of using the compounds and compositions.

2. Related Art

U.S. Pat. No. 4,326,055 discloses ethene derivatives which have a substituted phenyl ring and a substituted indane or tetrahydronaphtalene group. The compounds are described as tumor inhibiting agents, and useful for treating dermatological conditions and rheumatic illnesses.

U.S. Pat. No. 4,723,028 discloses 1,2 -diphenylethene (stilbene) derivataves which have retinoic acid-like activity.

U.S. Pat. No. 4,740,519 discloses certain aromatic heterocycle derivatives which have retinoic acid like activity.

Published European Patent Application 0 130795 discloses ethene derivatives, where the ethene moiety is substituted by a substituted phenyl group and by a substitituted chroman, thiochroman or quinoline group. The compounds are useful for inhibiting the degradation of cartilage in mammals.

European Patent Application 176034A (published Apr. 2, 1986) discloses tetrahydronaphtalene compounds having an ethynylbenzoic group. U.S. Pat. No. 4,739,098 discloses compounds wherein three olefinic units from the acid-containing moiety of retinoic acid are replaced by an ethynylphenyl functionality. These compound have retinoic acid-like biological activity.

U.S. Pat. No. 4,810,804 (issued on Mar. 7, 1989) based on an application of the same inventor and assigned to the same assignee as the present application, discloses such disubstituted acetylene compounds wherein one of the substituents of the acetylene (ethyne) group is a substituted phenyl group, and the second substituent is a 4,4-dimethyl substituted 6-chromanyl, 6-thiochromanyl or 6 -tetrahydroquinolinyl group. The compounds disclosed and claimed in U.S. Pat. No. 4,810,804 have retinoic acid-like biological activity.

A published European patent application of the present applicant (Publication No. 0284288, published on Sep. 28, 1988) describes compounds having retinoic acid like activity which are 4,4 dimethyl substituted chroman-6-yl, and 4,4 dimethyl-substituted thiochroman-6-yl acetylenes also substituted by a substituted heteroaryl group. This European application is based on the earliest of the "parent" applications of the present continuation-in-part application.

U.S. Pat. No. 4,980,369 describes compounds having retinoic acid like activity which are 2,2,4,4 tetraalkyl substituted chroman-6-yl, and 2,2,4,4 tetraalkyl substituted thiochroman-6-yl acetylenes also substituted by a substituted phenyl group.

Several co-pending applications and recently issued patents of the present inventor, which are assigned to the assignee of the present application, are directed to further compounds having retinoic acid-like activity. Among these U.S. Pat. No. 5,045,551 (issued on Sep. 3, 1991 and assigned to the same assignee as the present application) describes compounds having retinoic acid like activity which are 2,2,4,4 tetraalkyl substituted chroman-6-yl, and 2,2,4,4 tetraalkyl substituted thiochroman-6-yl acetylenes also substituted by a substituted heteroaryl group.

Retinoic acid-like activity has been generally recognized in the art to be associated with useful biological activity. Specifically, compounds having retinoic acid-like activity are useful as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic-cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopathy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

SUMMARY OF THE INVENTION

This invention covers compounds of Formula 1

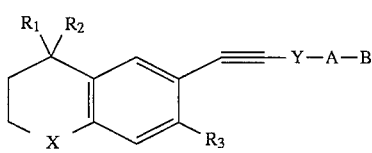

Formula 1 wherein $R_1$ and $R_2$, independently are n-alkyl groups having 2 to 8 carbons, or cyclo or branch-chained alkyl groups of 3 to 8 carbons;

$R_3$ is hydrogen or lower alkyl;

X is S, O or $N-R_4$ where $R_4$ is hydrogen or lower alkyl;

Y is phenyl or a heteroaryl group selected from a group consisting of thienyl, furyl, pyridazinyl, pyrimidinyl, pyrazinyl;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is hydrogen, COOH or a pharmaceutically acceptable salt thereof, COOR$_5$, CONR$_6$R$_7$, —CH$_2$OH, CH$_2$OR$_8$, CH$_2$OCOR$_8$, CHO, CH(OR$_9$)$_2$, CHOR$_{10}$O, —COR$_{11}$, CR$_{11}$(OR$_9$)$_2$, or CR$_{11}$OR$_{10}$O, where R$_5$ is an alkyl group of 1 to 10 carbons, or a cycloalkyl group of 5 to 10 carbons, or R$_5$ is phenyl or lower alkylphenyl, R$_6$ and R$_7$ independently are hydrogen, an alkyl group of 1 to 10 carbons, or a cycloalkyl group of 5 to 10 carbons, or phenyl or lower alkylphenyl, R$_8$ is alkyl of 1 to 10 carbons, phenyl or lower alkylphenyl, R$_9$ is lower alkyl, R$_{10}$ is divalent alkyl radical of 2–5 carbons and R$_{11}$ is an alkyl, cycloalkyl or alkenyl group containing 1 to 5 carbons.

In a second aspect, this invention relates to the use of the compounds of Formula 1 as regulators of cell proliferation and differentiation, and particularly as agents for treating dermatoses, such as acne, Darier's disease, psoriasis, icthyosis, eczema and atopic dermatitis, and for treating and preventing malignant hyperproliferative diseases such as epithelial cancer, breast cancer, prostatic cancer, head and neck cancer and myeloid leukemias, for reversing and preventing atherosclerosis and restenosis resulting from neointimal hyperproliferation, for treating and preventing other non-malignant hyperproliferative diseases such as endometrial hyperplasia, benign prostatic hypertrophy, proliferative vitreal retinopaythy and dysplasias, for treating autoimmune diseases and immunological disorders (e.g. lupus erythematosus), for treating chronic inflammatory diseases such as pulmonary fibrosis, for treating and preventing diseases associated with lipid metabolism and transport such as dyslipidemias, for promoting wound healing, for treating dry eye syndrome and for reversing and preventing the effects of sun damage to skin.

This invention also relates to a pharmaceutical formulation comprising a compound of Formula 1 in admixture with a pharmaceutically acceptable excipient.

In another aspect, this invention relates to the process for making a compound of Formula 1 which process comprises reacting a compound of Formula 2 with a compound of Formula 3 in the presence of cuprous iodide and Pd(PQ$_3$)$_2$Cl$_2$ (Q is phenyl) or a similar complex

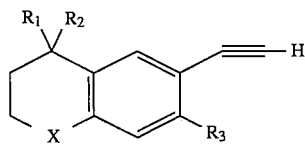

Formula 2

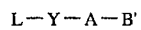

Formula 3 where A, R$_1$ through R$_3$, and Y are defined as above, L is a halogen, preferably I; and B' is H, or a protected acid, alcohol, aldehyde or ketone, where B' can be identical with B as defined above, or B' is such a precursor of the group B which is converted readily through a reaction or reactions well known by the practicing organic chemist into the group B of the compounds of the present invention.

Alternatively, this invention relates to the process for making a compound of Formula 1 which process comprises reacting a a zinc salt of Formula 4 with a compound of Formula 3 in the presence of Pd(PQ$_3$)$_4$ (Q is phenyl) or a similar complex. In Formula 4, R$_1$ through R$_3$ and X are defined as in connection with Formula 1 above.

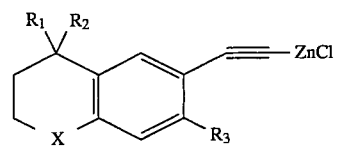

Formula 4

The present invention also relates to the process of converting a compound of Formula 1 into another compound of the same general formula, or converting a compound of Formula 5 into a compound of Formula 1, such conversion being performed through a reaction or reactions well within the skill of the practicing organic chemist, and including reactions such as: homologating an acid where A is (CH$_2$)$_{n'}$ where n' is 0–4 to give an acid of Formula 1; or converting an acid of Formula 1 to a salt; or forming an acid addition salt;

converting an acid of Formula 1 to an ester; or converting an acid of Formula 1 to an amide; or reducing an acid of Formula 1 to an alcohol or aldehyde; or converting an alcohol of Formula 1 to an ether or ester; or oxidizing an alcohol of Formula 1 to an aldehyde; or converting an aldehyde of Formula 1 to an acetal; or converting a ketone of Formula 1 to a ketal.

In Formula 5 all symbols are defined as above in connection with Formula 1 and Formula 3, as applicable.

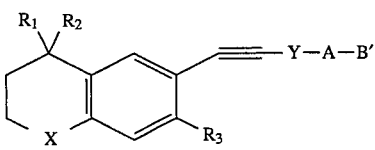

Formula 5

General Embodiments

Definitions

The term alkyl refers to and covers any and all groups which are known as normal alkyl, branch-chain alkyl and cycloalkyl. The term alkenyl refers to and covers normal alkenyl, branch chain alkenyl and cycloalkenyl groups having one or more sites of unsaturation. Lower alkyl means the above-defined broad definition of alkyl groups having 1 to 6 carbons, and as applicable, 3 to 6 carbons for branch chained and cyclo-alkyl groups. Lower alkenyl is defined similarly having 2 to 6 carbons for normal alkenyl, and 3 to 6 carbons for branch chained and cycloalkenyl groups.

The term "ester" as used here refers to and covers any compound falling within the definition of that term as classically used in organic chemistry. Where B (of Formula 1) is —COOH, this term covers the products derived from treatment of this function with alcohols, preferably with aliphatic alcohols having 1–6 carbons. Where the ester is derived from compounds where B is —CH$_2$OH, this term covers compounds of the formula —CH$_2$OOCR$_8$ where R$_8$ is any substituted or unsubstituted aliphatic, aromatic or aliphatic-aromatic group, preferably with 1–6 carbons in the aliphatic portions.

Preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids or alcohols. Also preferred are the phenyl or lower alkylphenyl esters.

Amide has the meaning classically accorded that term in organic chemistry. In this instance it includes the unsubstituted amides and all aliphatic and aromatic mono-and di-substituted amides. Preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from lower alkyl amines. Also preferred are mono- and di-substituted amides derived from the phenyl or lower alkylphenyl amines. Unsubstituted amides are also preferred.

Acetals and ketals include the radicals of the formula —CK where K is (—OR)$_2$. Here, R is lower alkyl. Also, K may be —OR$_1$O— where R$_1$ is lower alkyl of 2–5 carbon atoms, straight chain or branched.

A pharmaceutically acceptable salt may be prepared for any compound of this invention having a functionality capable of forming such salt, for example an acid or an amine functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used. Some of the compounds of the present invention (those where A is alkenyl) contain at least one double bond and therefore may have trans and cis (E and Z) isomers. In addition, some of the compounds of the present invention may contain one or more chiral centers and therefore exist in enantiomeric and diastereomeric forms. The scope of the present invention is intended to cover all such isomers per se, as well as mixtures of cis and trans isomers, mixtures of diastereomers and racemic mixtures of enantiomers (optical isomers) as well.

With respect to the groups R$_1$ and R$_2$ of Formula 1, the preferred compounds of the present invention are those where the R$_1$ and R$_2$ groups are identical with one another. Still more preferred are those compounds where R$_1$ and R$_2$ are normal alkyl having 2 to 6 carbons.

With respect to the R$_3$ group in Formula 1, the compounds are preferred where R$_1$ is hydrogen or methyl.

With regard to the heterocyclic portion of the compounds of the invention which bears the R$_1$ and R$_2$ groups, the thiochroman and chroman rings (X is S or O) are preferred. Between these two, still more preferred are the thiochroman derivatives (X is S).

With regard to the aromatic ring on the "other" side of the ethyne moeity of the compounds of the present invention, compounds are preferred where the aromatic ring is phenyl, pyridyl or thienyl. In other words, for the preferred compounds in Formula 1 the Y substituent is selected from a divalent phenyl, pyridyl or thienyl radical, and among these the phenyl and pyridyl derivatives are still more preferred. With regard to the substitution pattern on the phenyl group (when Y is phenyl) the compounds are preferred where the ethyne and A—B portions are 1,4 (para) to one another. The preferred substitution pattern on the pyridyl radical (when Y is pyridyl) is 2 and 5 in accordance with pyridine nomenclature (equivalent to 2 and 6 in accordance with nicotinic acid nomenclature.)

With regard to the A substituent on the phenyl or heteroaromatic ring, compounds are preferred where A is (CH$_2$)$_n$, and still more preferred where n is zero.

With respect to the symbol B, the compounds of the invention are preferred where B is —COOH, or an alkali metal salt or organic amine salt thereof. Alternatively, compounds are preferred where B is represented by COOR$_5$ (ester where R$_5$ is lower alkyl), CONR$_6$R$_7$ (amide) —CH$_2$OH (alcohol), CH$_2$OCOR$_8$, CH$_2$OR$_8$ (R$_8$ is lower alkyl; lower alkyl esters and ethers formed with a lower alkanol) or B is —CHO or CH(OR$_9$)$_2$, CHOR$_{10}$O (acetal derivatives), where R$_9$ and R$_{10}$ are defined as in connection with Formula 1. The most preferred compounds of the invention are shown in Formula 6.

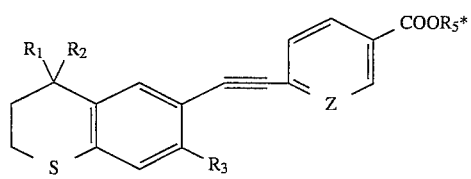

Formula 6

| Compound | | Z | |
|---|---|---|---|
| Compound 1 | R$_1$=R$_2$=CH$_3$CH$_2$— | Z = CH; | R$_{25}$* = ethyl; |
| Compound 2 | R$_1$=R$_2$=CH$_3$CH$_2$— | Z = CH; | R$_5$* = H; |
| Compound 3 | R$_1$=R$_2$=CH$_3$CH$_2$— | Z = N; | R$_5$* = ethyl; |
| Compound 4 | R$_1$=R$_2$=CH$_3$CH$_2$— | Z = N; | R$_5$* = H; |
| Compound 5 | R$_1$=R$_2$=CH$_3$(CH$_2$)$_2$— | Z = CH; | R$_5$* = ethyl; |
| Compound 6 | R$_1$=R$_2$=CH$_3$(CH$_2$)$_2$— | Z = CH; | R$_5$* = H; |
| Compound 7 | R$_1$=R$_2$=CH$_3$(CH$_2$)$_2$— | Z = N; | R$_5$* = ethyl; |
| Compound 8 | R$_1$=R$_2$=CH$_3$(CH$_2$)$_2$— | Z = N; | R$_5$* = H; |
| Compound 9 | R$_1$=R$_2$=CH$_3$(CH$_2$)$_2$— | Z = CH; | R$_5$* = ethyl; |
| Compound 10 | R$_1$=R$_2$=CH$_3$(CH$_2$)$_2$— | Z = CH; | R$_5$* = H; |
| Compound 11 | R$_1$=R$_2$=CH$_3$(CH$_2$)$_2$— | Z = N; | R$_5$* = ethyl; |
| Compound 12 | R$_1$=R$_2$=CH$_3$(CH$_2$)$_2$— | Z = N; | R$_5$* = H; |

The compounds of this invention may be administered systemically or topically, depending on such considerations as the condition to be treated, need for site-specific treatment, quantity of drug to be administered, and similar considerations.

In the treatment of dermatoses, it will generally be preferred to administer the drug topically, though in certain cases such as treatment of severe cystic acne, oral administration may also be used. Any common topical formulation such as a solution, suspension, gel, ointment, or salve and the like may be used. Preparation of such topical formulations are well described in the art of pharmaceutical formulations as exemplified, for example, *Remington's Pharmaceutical Science*, Edition 17, Mack Publishing Company, Easton, Pa. For topical application, these compounds could also be administered as a powder or spray, particularly in aerosol form.

If the drug is to be administered systemically, it may be confected as a powder, pill, tablet or the like, or as a syrup or elixir for oral administration. For intravenous or intraperitoneal administration, the compound will be prepared as a solution or suspension capable of being administered by injection. In certain cases, it may be useful to formulate these compounds in suppository form or as an extended release formulation for deposit under the skin or intermuscular injection.

Other medicaments can be added to such topical formulation for such secondary purposes as treating skin dryness, providing protection against light; other medications for treating dermatoses, preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the drug potentially could be used in a prophylactic manner to prevent onset of a particular condition. A given therapeutic concentration will vary from condition to condition and in certain instances may vary with the severity of the condition being treated and the patient's susceptibility to treatment. Accordingly, a given therapeutic concentration will be best determined at the time and place through routine experimentation. However, it is anticipated that in the treatment of, for example, acne, or other such dermatoses, that a formulation containing between 0.001 and 5 percent by weight, preferably about 0.01 to 1% will usually constitute a therapeutically effective concentration. If administered systemically, an amount between 0.01 and 100 mg per kg body weight per day, but preferably about 0.1 to 10 mg/kg, will effect a therapeutic result in most instances.

The retionic acid like activity of these compounds was confirmed through the classic measure of retionic acid activity involving the effects of retionic acid on ornithine decarboxylase. The original work on the correlation between retinoic acid and decrease in cell proliferation was done by Verma & Boutwell, *Cancer Research*, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all causes for ODC activity increase are unknown, it is known that 12-O-tetradecanoyl-phorbol-13-acetate (TPA) induces ODC activity. Retinoic acid inhibits this induction of ODC activity by TPA. The compounds of this invention also inhibit TPA induction of ODC as demonstrated by an assay essentially following the procedure set out in *Cancer Res.*, 35: 1662–1670, 1975.

By way of example of retinoic acid-like activity it is noted that in the assay conducted essentially in accordance with the method of Verma & Boutwell, ibid, the following examples of the preferred compounds of the present invention (Compounds 3, 7 and 11) attained an 80% inhibition of TPA induced ODC activity at the following concentrations ($IC_{80}$):

| Compound | $IC_{80}$ conc (nmols) |
|---|---|
| 3 | 0.3 |
| 7 | 2.5 |
| 11 | 0.6 |

Specific Embodiments

The compounds of this invention can be made by a number of different synthetic chemical pathways. To illustrate this invention, there is here outlined a series of steps which have been proven to provide the compounds of Formula 1 when such synthesis is followed in fact and in spirit. The synthetic chemist will readily appreciate that the conditions set out here are specific embodiments which can be generalized to any and all of the compounds represented by Formula 1. Furthermore, the synthetic chemist will readily appreciate that the herein described synthetic steps may be varied and or adjusted by those skilled in the art without departing from the scope and spirit of the invention.

Reaction Scheme 1

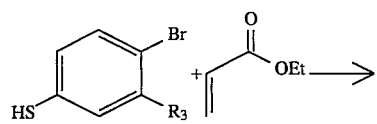

Formula 7

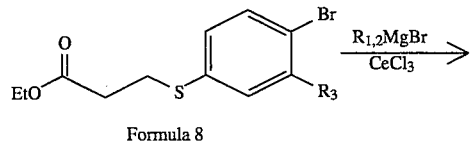

Formula 8

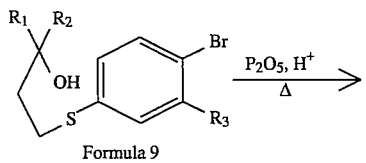

Formula 9

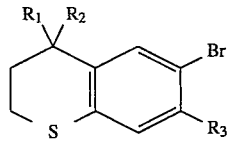

Formula 10

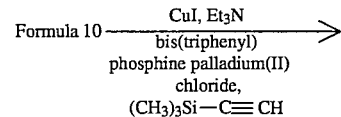

-continued
Reaction Scheme 1

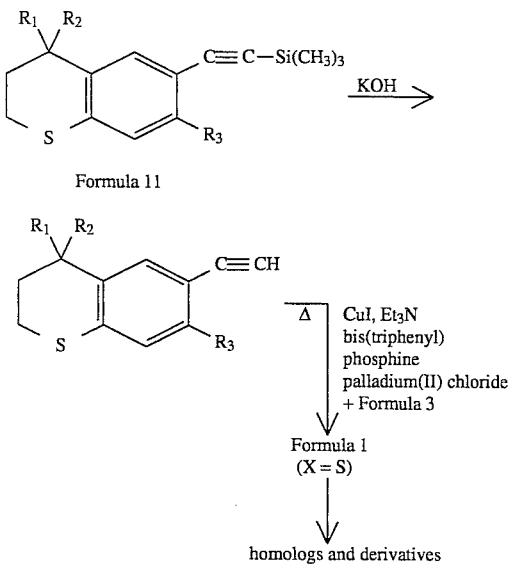

Formula 11

Formula 1
(X = S)

↓ homologs and derivatives

The thiochroman derivatives of the present invention, that is compounds of Formula 1 where X is S, are prepared in accordance with Reaction Scheme 1. In accordance with this sequence of reactions, a 4-bromothiophenol derivative of Formula 7 is reacted with ethyl acrylate to provide the ethyl 3-(4-bromophenylthio)propionate derivative of Formula 8. In this reaction scheme the symbol $R_3$ has the same definition as in Formula 1 above. It follows from the foregoing that when $R_3$ is H, then the starting material of the reaction sequence is 4-bromothiophenol; when $R_3$ is methyl, for example, then the starting material of Formula 7 is 3-methyl-4-bromothiophenol. To introduce the $R_1$ and $R_2$ substituents into the compounds of the invention the ethyl 3-(4-bromophenylthio)propionate derivative of Formula 8 is reacted with a Grignard reagent, such as ethyl-, n-propyl-, and n-butylmagnesium bromide. The Grignard reaction is preferably conducted in the presence of cerium trichloride ($CeCl_3$). In Reaction Scheme 1 the Grignard reagent is denoted as "$R_{1,2}$" to signify that both the $R_1$ and the $R_2$ groups can be introduced in this manner, and that in the preferred embodiments these groups are identical with one another. The product of the Grignard reaction is the tertiary alcohol of Formula 9 which is thereafter cyclized (under Friedel Crafts like conditions, such as in the presence of phosphorous pentoxide and methanesulfonic acid) to provide the 6-bromo-4,4-dialkylthiochroman derivative of Formula 10. The compound of Formula 10 is thereafter reacted with trimethylsilylacetylene in the presence of cuprous iodide (CuI) and a suitable catalyst, typically having the formula $Pd(PQ_3)_2Cl_2$ (Q is phenyl). The reaction is typically conducted in the presence of bis(triphenylphosphine)palladium(II) chloride catalyst, an acid acceptor (such as triethylamine) under an inert gas (argon) atmosphere by heating in a sealed tube. The trimethylsilyl group is removed from the resulting (4,4-dialkylthiochroman-6-yl)-trimethylsilylacetylene derivative of Formula 11 under basic conditions to provide the (4,4-dialkylthiochroman-6-yl)-acetylene derivative of Formula 12.

In order to introduce the phenyl or heteroaryl substituent on the acetylene (ethyne) portion of the compounds of Formula 12, the compound is coupled with the reagent L—Y—A—B' (Formula 3) where the symbols L, Y, A and B' have the same meaning as defined in connection with Formula 3. In other words, the phenyl or heteroaryl substituent is introduced into the 6-thiochromanylacetylene of Formula 12 by reacting the latter with a halogen substituted phenyl compound or heteroaromatic compound (Formula 3) in which the aromatic nucleus (Y) either has the desired substituent [A—B], or wherein the actual substituent A—B' can be readily converted to the desired substituent by means of organic reactions well known in the art.

Coupling of the 4,4,-dialkyl-6-thiochromanyl acetylene of Formula 12 with the reagent L—Y—A—B' (Formula 3) is affected directly in the presence of cuprous iodide, a suitable catalyst, typically of the formula $Pd(PQ_3)_2Cl_2$ (Q is phenyl) and an acid acceptor, such as triethylamine, by heating in a sealed tube under an inert gas (argon) atmosphere.

The resulting disubstituted acetylene compound (Formula 1, X=S) may be the target compound made in accordance with the invention, or maybe readily converted into the target compound by such steps as salt formation, esterification, deesterification, homologation, amide formation and the like. These steps are further discussed below.

The disubstituted acetylene compound (Formula 1, X=S) may also be obtained by first converting the 4,4-dialkyl-6-thiochromanyl acetylene derivative of Formula 12 into the corresponding metal salt, such as a zinc salt, and thereafter coupling the zinc salt with the reagent L—Y—A—B' (Formula 3) in the presence of a catalyst having the formula $Pd(PQ_3)_4$ (Q is phenyl), or similar complex.

Derivatization of Compound 18 is indicated in Reaction Scheme 1 as conversion to "homologs and derivatives".

More specifically with respect to either derivatization or deblocking of protected functionalities, or with respect to the preparation of compounds of the formula L—Y—A—B' (Formula 3), (which after coupling either directly yield the compounds of the invention, or are readily converted into them) the following is noted.

Where a protected phenyl or heteroaromatic compound is needed to couple with the compounds of Formula 2, such may be prepared from their corresponding acids, alcohols, ketones or aldehydes. These starting materials, the protected acids, alcohols, aldehydes or ketones, are all available from chemical manufacturers or can be prepared by published methods. Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide and dimethylaminopyridine. The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

To increase the value of n before effecting a coupling reaction, where such compounds are not available from a commercial source, the pheny or heteroaromatic derivatives where B is —COOH are subjected to homologation by successive treatment under Arndt-Eistert conditions or other homologation procedures. Alternatively, phenyl or heteroaromatic derivatives where B is different from COOH, may also be homologated by appropriate procedures. The homologated acids can then be esterified by the general procedure outlined in the preceding paragraph.

An alternative means for making compounds of Formula 1 where A is (CH$_2$)$_n$ and n is 1–5, is to subject the compounds of Formula 1, where B is an acid or other function, to homologation, using the Arndt-Eistert method referred to above, or other homologation procedures.

The acids and salts derived from Formula 1 are readily obtainable from the corresponding esters. Basic saponification with an alkali metal base will provide the acid. For example, an ester of Formula 1 may be dissolved in a polar solvent such as an alkanol, preferably under an inert atmosphere at room temperature, with about a three molar excess of base, for example, potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the acid is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert inorganic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alky halides under Williamson reaction conditions (March, Ibid, pg. 357) gives the corresponding ethers. These alcohols can be converted to esters by reacting them with appropriate acids in the presence of acid catalysts or dicyclohexlcarbodiimide and dimethlaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/ oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

Compounds where B is H can be prepared from the corresponding halogenated aromatic compound (preferably where the halogen is I) by hydrogenation.

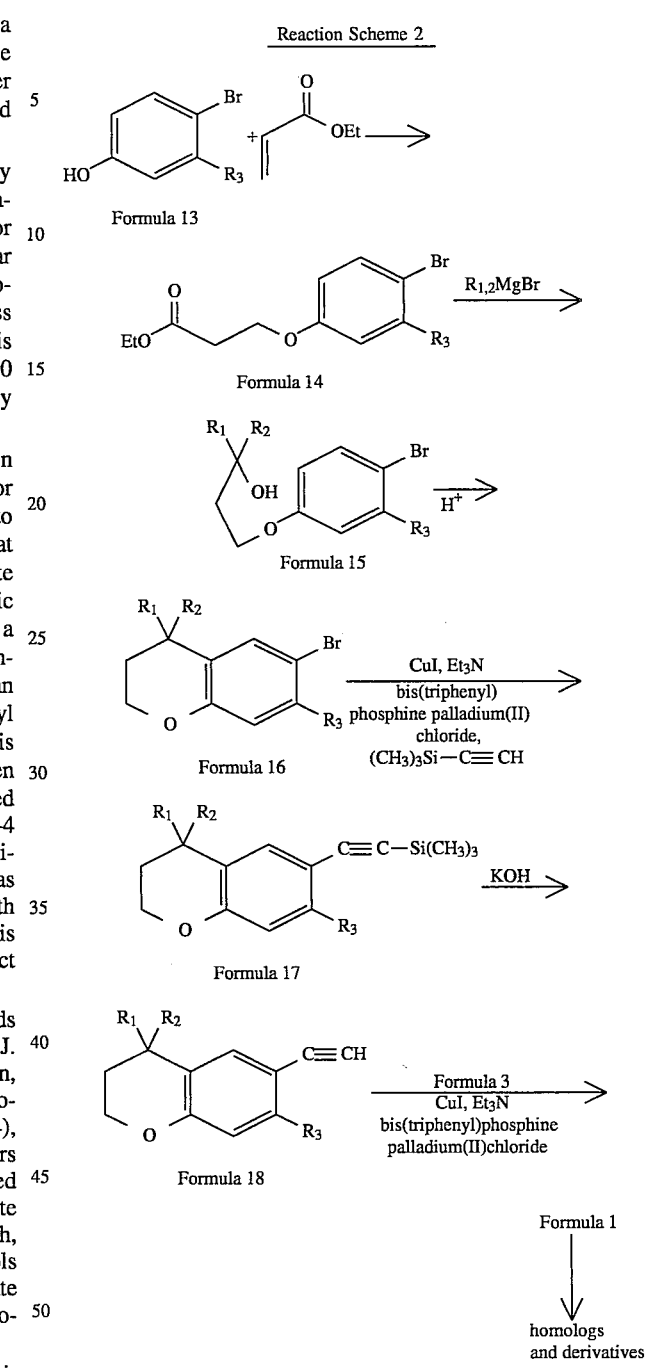

The chroman derivatives of the present invention (compounds of Formula 1 where X is O) can be prepared in a reaction sequence which is similar to the reaction sequence used for preparing the thiochroman derivatives, with the major difference being that instead of a suitable thiophenol derivative the corresponding phenol derivative is used as a starting material. Thus, with reference to Reaction Scheme 2, the 4-bromophenol derivative of Formula 13 is reacted with ethylacrylate to provide the ethyl 3-(4-bromophenyl-)propionate derivative of Formula 14. (The symbol R$_3$ has the same definition as in Formula 1 above; when R$_3$ is H, then the starting material of the reaction sequence is 4-bromophenol; when R$_3$ is methyl then the starting material of Formula 13 is 3-methyl-4-bromophenol.) To introduce the $R_1$ and $R_2$ substituents into the compounds of the invention the ethyl 3-(4 -bromophenyl)propionate derivative of Formula 14 is reacted with a Grignard reagent, such as ethyl-, n-propyl-, and n-butylmagnesium bromide. As in the previous reaction scheme in this scheme also, the Grignard reagent is denoted as "$R_{1,2}$" to signify that both the $R_1$ and the $R_2$ groups can be introduced in this manner, and that these groups are identical with one another in the preferred embodiments. The product of the Grignard reaction is the tertiary alcohol of Formula 15 which is thereafter cyclized (under Friedel Crafts like conditions) to provide the 6-bromo-4,4 -dialkylchroman derivative of Formula 16. The compound of Formula 16 is thereafter reacted with trimethylsilylacetylene in the presence of cuprous iodide (CoI) and a suitable catalyst, typically having the formula $Pd(PQ_3)_2Cl_2$ (Q is phenyl). As the reaction of the corresponding thiochromans (Formula 10) this reaction also is typically conducted in the presence of bis(triphenylphosphine)palladium(II) chloride catalyst, an acid acceptor (such as triethylamine) under an inert gas (argon) atmosphere by heating in a sealed tube. The trimethylsilyl group is removed from the resulting (4,4-dialkylchroman-6-yl)-trimethylsilylacetylene derivative of Formula 17 under basic conditions to provide the (4,4-dialkylchroman-6-yl)-acetylene derivative of Formula 18. The compound of Formula 18 is thereafter coupled with the reagent L—Y—A—B' (Formula 3). In analogy to the coupling of the corresponding thiochroman compounds of Formula 12 with the compounds of Formula 3, the coupling of the 4,4,-dialkyl-6 -chromanyl acetylene of Formula 18 with the reagent L—Y—A—B' (Formula 3) is also conducted in the presence of cuprous iodide, a suitable catalyst, typically of the formula $Pd(PQ_3)_2Cl_2$ (Q is phenyl) and an acid acceptor, such as triethylamine, by heating in a sealed tube under an inert gas (argon) atmosphere.

The resulting disubstituted acetylene compound (Formula 1, X=O) may be the target compound made in accordance with the invention, or maybe readily converted into the target compound by such steps as salt formation, esterification, deesterification, homologation, amide formation and the like.

An alternative method for preparing the compounds of Formula 1 where X=O, and specifically for preparing the intermediate of Formula 18 which is suitable for coupling with the reagent L—Y—A—B' (Formula 3) is a modification of the procedure disclosed in U.S. Pat. No. 4,810,804 and depicted in Reaction Scheme 2 of that patent. For this reason, the specification of U.S. Pat. No. 4,810,804 is expressly incorporated herein by reference. The procedure as applied to compounds of Formula 1 where $R_1$ and $R_2$ would be methyl, is also disclosed in the parent of the present continuation-in-part application Ser. No. 07/326, 191, filed on Mar. 20, 1989, expected to be issued as U.S. Pat. No. 5,089,509. The sequence of reactions according to this procedure is shown in Reaction Scheme 3 and is summarized below.

Reaction Scheme 3

$(QO)_2POCl + R_2'CH=CR_1-CH_2-CH_2OH \longrightarrow$

Formula 19

-continued
Reaction Scheme 3

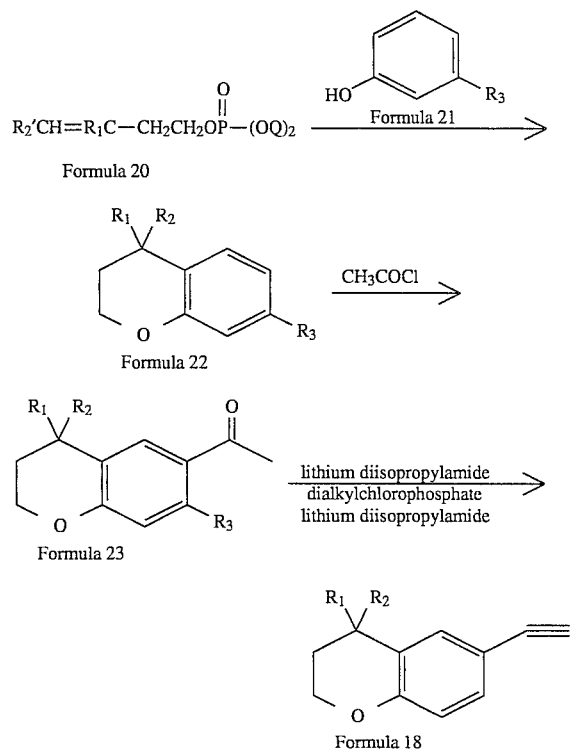

Thus, diphenyl chlorophosphate indicated as $(QO)_2POCl$ (commercially available e.g. from Aldrich, or prepared by means known in the art) and the alcohol of Formula 19 are reacted to form the phosphate of Formula 20. In the structure of the alcohol of Formula 19 $R_1$ is defined as in connection with Formula 1, and $R_2'$ is defined as an alkyl group one carbon shorter than the $R_2$ group defined above in connection with Formula 1. In other words, where as in the most preferred compounds of the invention $R_2$ is respectively ethyl, n-propyl and n-butyl, the $R_2'$ group of the alcohol of Formula 19 is respectively methyl, ethyl, and n-propyl. The unsaturated alcohol of Formula 19 can be prepared in accordance with procedures known in the art. A preferred method for preparing the phosphate of Formula 20 is to dissolve the alcohol of Formula 19 in an excess of pyridine or the like under an inert atmosphere cooled to approximately $-10$ degrees to 10 degrees C. This solution is then added drop-wise, under an inert atmosphere, to a solution of diphenyl chlorophosphate in about an equal amount of the reaction solvent. About a 2–5% molar excess of diphenyl chlorophosphate relative to the alcohol of Formula 19 is employed. Thereafter, the mixture is heated until the formation of the phosphate ester of Formula 20 is substantially completed. The product is then recovered by conventional means. The diphenyl phosphate ester (Formula 20) is then reacted with a phenol derivative of Formula 21 to effect formation of the 4,4-dialkylchroman of Formula 22. For the synthesis of the compounds of the invention where $R_3$ is hydrogen, unsubstituted phenol is the reagent of Formula 21. In the event $R_3$ is methyl, for example, then the reagent of Formula 21 is 3-methylphenol. Exemplary conditions for the reaction of the phenol of Formula 21 and the phosphate of Formula 20 are as follows. The phenol or substituted phenol is added to a flask already containing stannic chloride which has been cooled to between $-10$ degrees to 10 degrees C.

After thorough mixing of this combination at the reduced temperature, the phosphate ester (Formula 20) is added at the reduced temperature. Both of these steps are carried out under an inert atmosphere such as argon or nitrogen. When the addition of the phosphate ester of Formula 20 is completed, the mixture is stirred at about ambient temperature for up to 24 hours. Then the reaction is quenched with a dilute solution of aqueous alkali metal base or the like. The product 4,4-dialkylchroman of Formula 22 is recovered by extraction and other conventional means.

The acetylenic (ethynyl) function is introduced into the 4,4-disubstituted (and optionally 7 -substituted) chroman (Formula 22) by acetylation with acetyl chloride (to yield the compounds of Formula 23), and thereafter the acetyl group is converted to the ethynyl group through treatment with lithium diisopropylamide, dialkyl chlorophosphate and another treatment with lithium diisopropylamide. The generalized conditions (and likely reaction mechanisms) for these latter transformation which yield the 4,4-dialkyl-6-chromanyl acetylene compounds of Formula 18 are as follows. The compound of the Formula 22 is acetylated under Fridel Crafts conditions, or the like, preferably with acetyl chloride (AlCl$_3$, CH$_2$Cl$_2$, reflux) to provide the 4,4-dialkyl-6-acetyl-chroman of Formula 23. The acetyl function of the compound of Formula 23 is converted into an acetylenic (ethynyl) function by means of lithium diisopropylamide, or a similar base, at reduced temperature. An intermediate derived from the compound of Formula 23 (presumably a lithium salt of the corresponding enol, not shown on Reaction Scheme 3) is esterified by treatment with diethychlorophosphate (or the like) and is again reacted at reduced temperature (e.g. −78 degrees C.) with lithium diisopropylamide, to form the triple bond (presumably by an elimination reaction) and to yield the 4,4-dialkyl-6-chromanyl acetylene derivative (Formula 18).

It is noted at this point that the present invention is not intended to be limited or bound by the above-mentioned and other theories of reaction mechanisms. Brief description of theory of reaction mechanisms (where applicable) are given to further enable and facilitate the work of a skilled artisan in the field to modify and adjust the synthetic conditions to fit particular specific intermediates and to make the several compounds of the invention, without departing from the scope and spirit of the invention.

The 4,4-dialkyl-6-chromanyl acetylene obtained in this manner is coupled with the reagent of Formula 3 as indicated in Reaction Scheme 2. The generalized conditions of this coupling are described above. Alternatively, the compounds of Formula 18 are first converted to the corresponding zinc salt, and are then utilized as such in the coupling reaction with the reagent of Formula 3. In general terms, the formation of the zinc salts is conducted under conditions which exclude water and oxygen. A dry, ether-type solvent such as dialkyl ether or a cyclic ether such as a furan or pyran, particularly a tetrahydrofuran, may be used as the solvent. A solution of the compound of Formula 18 is first prepared under an inert atmosphere (argon or nitrogen) and then a strong base such as n-butyl lithium is added (in about a 10% molar excess). This reaction is begun at a reduced temperature of between −10 degrees and +10 degrees C., preferably about 0 degrees C. The reaction mixture is stirred for a short period, between 30 minutes and 2 hours, and then treated with about a 10% molar excess of fused zinc chloride dissolved in the reaction solvent. This mixture is stirred for an additional 1–3 hours at about the starting temperature, then the temperature is increased to about ambient temperature for 10–40 minutes.

The foregoing general description for the preparation of the ZnCl salts of compounds symbolized by Formula 18, are also applicable, with such modifications which will be readily apparent to the skilled artisan in the field, to the preparation of all ZnCl salts of the appropriate acetylene (ethyne) intermediates leading to the compounds of the present invention.

A synthetic sequence which is suitable for preparing the compounds of Formula 1 where X=NR$_4$, and specifically for preparing a 4,4-dialkyl-6 -tetrahydroquinolinyl acetylene intermediate which is suitable for coupling with the reagent L—Y—A—B' (Formula 3) is a modification of the procedure disclosed in U.S. Pat. No. 4,810,804 and depicted in Reaction Scheme 3 of that patent. The procedure as applied to compounds of Formula 1 where R$_1$ and R$_2$ would be methyl, is also disclosed in the parent of the present continuation-in-part application Ser. No. 07/326,191, filed on Mar. 20, 1989, expected to be issued as U.S. Pat. No. 5,089,509. The sequence of reactions according to this procedure, which itself follows a procedure of European Patent Application 0130795 (published Sep. 1, 1985) is shown in Reaction Scheme 4 and is summarized below.

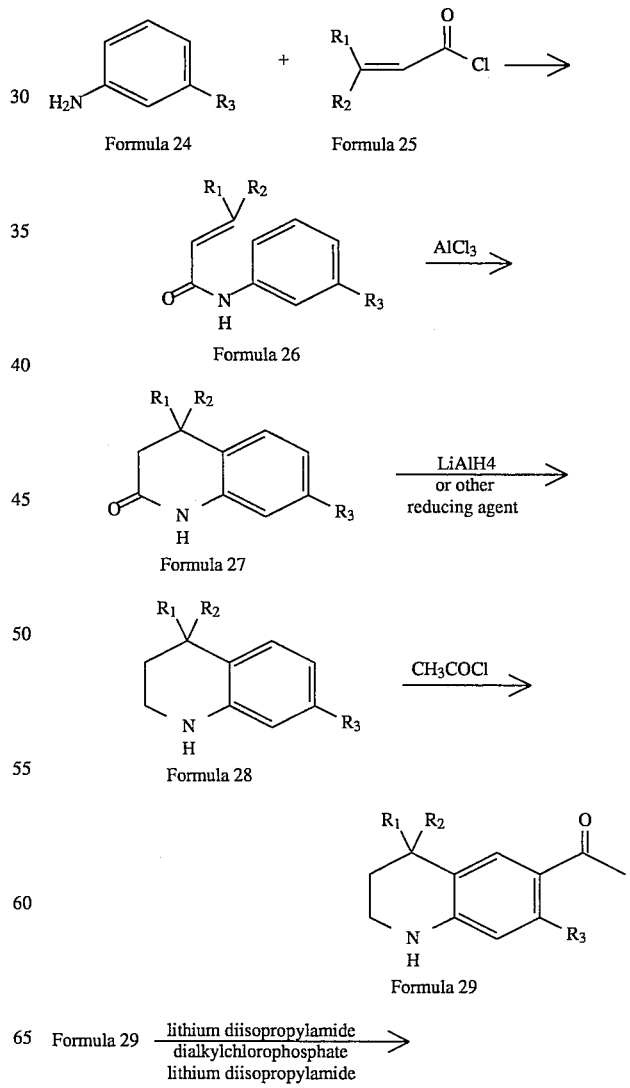

Reaction Scheme 4

-continued
Reaction Scheme 4

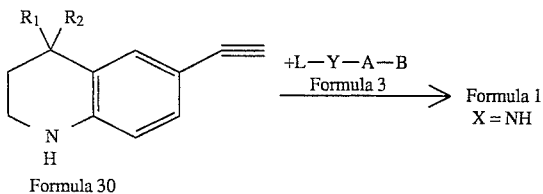

Reaction Scheme 4

Thus, with reference to Reaction Scheme 4, the reaction sequence is hereinafter described with primary emphasis to preferred embodiments where $R_4$ (of Formula 1) is hydrogen. Thus, the aniline derivative of Formula 24 is first acylated with the acyl chloride of the Formula 25. In the event $R_3$ is hydrogen, the starting material of Formula 24 is unsubstituted aniline. The acyl chloride (Formula 25) carries the $R_1$ and $R_2$ substituents of on its unsaturated carbon, in the β position. For the most preferred embodiments $R_1$ and $R_2$ are respectfully ethyl, n-propyl and n-butyl. Such acid chlorides can be synthesized in accordance with procedures known in the art. The amide of Formula 26 is then cyclized under Friedel-Crafts type reaction conditions (aluminum chloride) to give the 2-oxo-1,2,3,4-tetrahydroquinoline derivatives of Formula 27. Lithium aluminum hydride or another acceptable reducing agent of similar type is then used to reduce the compounds of Formula 27, (preferably in inert solvent such as diethyl ether). In order to introduce the acetyl (ethyne) group into the 6-position of the 4,4-dialkyl-tetrahydroquinoline derivative of Formula 28, the compound is N-acetylated using acetyl chloride (in a polar solvent such as pyridine) followed by acetylation under Friedel Crafts type conditions (aluminum chloride) to give an intermediate which is thereafter subjected to base hydrolysis to remove the N-acetyl group and give compounds of Formula 29.

The 6-acetyl group of the compounds of Formula 29 is thereafter converted into an ethynyl group in the manner described above for analogous transformation of 4,4-dialkyl-6-acetyl chromans. The 4,4 dialkyl-6 -ethynyl 1,2,3,4-tetrahydroquinoline (Formula 30) may be coupled directly or as the corresponding ZnCl salt, with compounds of Formula 3.

Alternatively compounds of Formula 1 where X= is $NR_4$ can also be prepared by starting from the corresponding 4-bromo-aniline derivative, in analogy to the sequence outlined in Reaction Scheme 4 up to the step of obtaining the 6-bromo analog of the compound of Formula 28. Thereafter, the acetylene (ethyne) group is introduced into the molecule in analogy to the corresponding steps outlined in Reaction Scheme 1. These steps will be self-evident to those skilled in the art in light of the analogous reactions disclosed above.

The following examples of specific compounds of the invention, and specific examples of the synthetic steps in which the compounds and certain intermediates are made, are set out to illustrate the invention, not to limit its scope.

Specific Examples

Ethyl 6-chloronicotinate (Compound 20)

A mixture of 15.75 g (0.1 mol) 6-chloronicotinic acid, 6.9 g (0.15 mol) ethanol, 22.7 g (0.11 mol) dicyclohexylcarbodiimide and 3.7 g dimethylaminopyridine in 200 ml methylene chloride was heated at reflux for 2 hours. The mixture was allowed to cool, solvent removed in vacuo and residue subjected to flash chromatography to give the title compound as a low-melting white solid. PMR (CDCl$_3$): δ1.44 (3H, t, J~6.2 Hz) 4.44 (2H, q, J~4.4 Hz), 7.44 (1H, d, J~8.1 Hz), 8.27 (1H, dd, J~8.1 Hz, 3 Hz), 9.02 (1H, d, J~3 Hz).

The foregoing procedure may be used to esterify any of the other halo-substituted acids employed in the making of these compounds such as:

ethyl 2-(2-chloropyrid-5-yl)acetate;
ethyl 5-(2-chloropyrid-5-yl)pentanoate;
ethyl 2-(2-iodofur-5-yl)acetate;
ethyl 5-(2-iodofur-5-yl)pentanoate;
ethyl 2-(2-iodothien-5-yl)acetate;
ethyl 5-(2-iodothien-5-yl)pentanoate;
ethyl 2-(3-chloropyridazin-6-yl)acetate;
ethyl 5-(3-chloropyridazin-6-yl)pentanoate; and
the corresponding chloro, or other halo, substituted pyrimidinyl or pyrazinyl analogues of such esters. The just mentioned esters (including ethyl-chloronicotinate, and ethyl-6-iodomicotinate can serve as the reagents, for coupling with the corresponding ethynyl compounds or their zinc salts to provide the target compounds of the invention.

6-Iodo-nicotinic acid

A mixture of 15.962 g ((0.106 mol) of sodium iodide in 51 g (30 ml, 40 mmol) of hydriodic acid were stirred for 5 minutes. To the mixture was added 17.184 g (0.109 mol) of 6-chloro-nicotinic acid and the resulting mixture refluxed at 100–130 C.°C. for 40 hours. The dark brown mixture was then taken up in 300 ml of acetone and stirred to dissolve the excess NaI. The product was collected by suction filtration, rinsed with 100 mL in 1N NaHSO$_3$ and dried to give the title compound as a yellow solid.

PMR (DMSO-d$^6$): δ3.36 (1H, s), 7.89 (1H, dd, J=2.5, 8.2 Hz), 8.00 (1H, d, J=7.5 Hz), 8.79 (1H, d, J=2.4 Hz).

Ethyl 6-Iodo-nicotinoate (Compound 21)

A mixture of 16.230 g (84.5 mmol) of 1-(3 -dimethylaminopropyl)-3-ethylcarbodiimide hydrochloride in 90 ml of methylene chloride was cannulated into a mixture of 17.80 g (71.2 mmol) of 6-iodo-nicotinic acid in 30 ml of methylene chloride. The resulting mixture was stirred and 7.85 g (0.171 mmol) of ethanol, and then 0.826 g (6.8 mmol) of 4-dimethylaminopyridine was added and the resulting mixture refluxed at 55° C. for 20 hours and then stirred at room temperature for 12 hours. Ether and water were added and the layers separated. The aqueous layer was extracted with 2×40 ml of ether and the organic portions combined, washed with saturated NaCl, dried over Na$_2$SO$_4$, and concentrated yielding a white solid which was purified by flash chromatography (SiO$_2$, 10% ethyl acetate in hexanes) to give the title compound as a white solid.

PMR (CDCl$_3$): δ1.41 (3H, t, J=7.1 Hz), 4.41 (2H, q, J=7.1 Hz), 7.83 (1H, d, J=8.2 Hz), 7.89 (1H, dd, J=2.4, 8.2 Hz), 8.93 (1H, d, J=2.1 Hz).

Ethyl-4-iodobenzoate (Compound 22)

To a suspension of 10 g (40.32 mmol) of 4 -iodobenzoic acid in 100 ml absolute ethanol was added 2 ml thionyl chloride and the mixture was then heated at reflux for 3 hours. Solvent was removed in vacuo and the residue was dissolved in 100 ml ether. The ether solution was washed with saturated NaHCO$_3$ and saturated NaCl solutions and dried (MgSO$_4$). Solvent was then removed in vacuo and the residue kugelrohr distilled (100 degrees C.; 0.55 mm) to give the title compound as a colorless oil, PMR (CDCl$_3$): δ1.42 (3H, t, J~7 Hz), 4,4 (2H, q, J~7 Hz), 7.8 (4H).

In the same manner, but substituting for 4-iodobenzoic acid the appropriate acid, the following examples of compounds can be prepared:

ethyl 4-iodophenylacetate;

ethyl 3-(4-iodophenyl)propionate;

ethyl 4-(4-iodophenyl)butanoate; and ethyl 5-(4-iodophenyl)pentanoate.

Ethyl 3-(4-bromophenylthio)propionate (Compound 23)

To a solution of 10.4 g (55.2 mmol) of 4-bromothiophenol and 6.49 g (55.4 mmol of ethyl acrylate in 5 mL of dichloromethane was added 4.13 g (41 mmol) of triethylamine at 0° C. under argon. The resulting solution was warmed to room temperature and stirred for 12 hours. The solution was then treated with 50 mL 10% aqueous NaOH and the product extracted into 3×100 mL ether.

The combined ether extracts were washed with saturated aqueous NaCl, dried (MgSO$_4$), filtered and the solvent removed under reduced pressure. The residue was purified by flash chromatography (SiO2, 10% ethyl acetate in hexanes) to give the title compound as a white solid.

PMR (CDCl$_3$): δ1.26 (3H, t, J=7.1 Hz), 2.61 (2H, t, J=7.4 Hz), 3.15 (2H, t, J=7.5 Hz), 4.15 (2H, q, J=7.2 Hz), 7.24 (2H, dd, J=6.4, 8.5 Hz), 7.43 (2H, dd, J=6.4, 8.5 Hz).

3-Ethyl-5-(4-bromophenylthio)-3-pentanol (Compound 24)

To a stirred suspension of 20 g (81 mmol) of cerium trichloride in 50 mL of tetrahydrofuran was added 19.9 g of ethylmagnesium bromide (35 mmol, 1M in THF). The resulting mixture was stirred for 1 hour and then cooled to 0° C. A solution of 4.71 g (17.36 mmol) of ethyl 3-(4-bromophenylthio)propionate (Compound 23) in 25 mL of tetrahydrofuran was then cannulated into the cool mixture and the resulting suspension stirred at room temperature for 16 hours. The reaction mixture was then cooled to 0° C. and treated with 200 mL of water and extracted with 5×50 mL of ether.

The ether extracts were combined and washed successively with 2×20 mL of saturated aqueous NaCl and dried (Na$_2$SO$_4$). The solvent was removed in-vacuo and the residue purified by flash chromatography (SiO$_2$, 10% ethyl acetate in hexanes) to give the title compound as an orange oil.

PMR (CDCl$_3$): δ0.86 (6H, t, J=7.6 Hz), 1.49 (4H, q, J=7.4 Hz), 1.74 (2H, m), 2.05 (1H, s), 2.96 (2H, m), 7.21 (2H, dd, J=2.0, 6.5 Hz), 7.41 (2H, dd, J=2.0, 6.5 Hz).

6-Bromo-4,4-diethylthiochroman (Compound 25)

A mixture of 1.18 g (8.3 mmol) of phosphorus pentoxide in 10 mL of methanesulfonic acid was heated for 45 minutes at 75° C. The solution was allowed to cool slightly and 2.58 g (8.5 mmol) of 3-ethyl-5-(4-bromophenylthio)-3-pentanol (Compound 24) was added. The resulting mixture was stirred at room temperature for 2 hours. The mixture was then cooled to 0° C. and treated with 50 mL of water and extracted with 3×50 mL of ether.

The ether extracts were combined and washed with saturated aqueous NaCl and then dried (Na$_2$SO$_4$). The solvent was removed in-vacuo and the residual oil purified by flash chromatography (SiO$_2$, 10% ethyl acetate in hexanes) to give the title compound as an orange oil.

PMR (CDCl$_3$): δ0.78 (6H, t, J=7.5 Hz), 1.66 (4H, m), 1.94 (2H, m), 2.98 (2H, m), 6.96 (1H, d, J=8.4 Hz), 7.12 (1H, dd, J=2.3, 8.6 Hz), 7.30 (1H, d, J=2.2 Hz).

(4,4-Diethylthiochroman-6-yl)(trimethylsilyl)acetylene (Compound 26)

A mixture of 1.96 g (6.90 mmol) of 6-bromo-4,4-diethylthiochroman (Compound 25), 0.11 g (0.59 mmol) of copper (I) iodide and 4.36 g (4.31 mmol) of triethylamine was degassed with argon for 15 minutes at −78° C. To the suspension was added 6.95 g (71 mmol) of (trimethylsilyl)acetylene then 0.41 g (58 mmol) of bis(triphenylphosphine)palladium (II) chloride. The solution was degassed with argon for an additional 5 minutes and the resulting mixture was allowed to warm to 0° C. The tube was sealed and the mixture heated to 55° C. for 15 hours.

The mixture was allowed to cool to room temperature and was filtered through celite and silica gel using 200 mL of hexane. The solvent was removed in-vacuo and the residual oil purified by flash chromatography (SiO$_2$, 100% hexane) to give the title compound as an orange oil.

PMR (CDCl$_3$): δ0.00 (9H, s), 0.79 (6H, t, J=7.7 Hz), 1.69 (4H, m), 1.95 (2H, m), 3.00 (2H, m), 6.96 (1H, δ, H=8.4 Hz), 7.13 (1H, dd, J=2.2, 8.3 Hz), 7.30 (1H, d, J=2.2 Hz).

(4,4-Diethylthiochroman-6-yl)acetylene (Compound 27)

A solution of 2.21 g (39 mmol) of potassium hydroxide in 2.0 mL of water and 20.0 mL of ethanol was added to 1.49 g (4.93 mmol) of (4,4-diethylthiochroman-6-yl)(trimethylsilyl)acetylene (Compound 26) and the resulting mixture stirred at room temperature for 5 hours during which time it became homogeneous. The solvent was removed in-vacuo and the residue was acidified with 5% aqueous H$_2$SO$_4$. The product was extracted with 2×50 mL of ether.

The combined ether extracts were washed successively with 10% aqueous NaHCO$_3$ and saturated aqueous NaCl. The solvent was removed in-vacuo and the residue purified by Kugelrohr distillation (135° C., 0.75 mm) to give the title compound as an orange oil.

PMR (CDCl$_3$): δ0.79 (6H, t, J=7.6 Hz), 1.68 (4H, m), 1.96 (2H, m), 3.02 (3H, overlapping m, s), 7.04 (1H, d, J=8.1 Hz), 7.14 (1H, dd, J=7.1, 8.2 Hz), 7.32 (1H, s).

Ethyl-2-[2-(4,4-diethylthiochroman-6-yl)-ethyn-1-yl]-5-nicotinate (Compound 3)

A mixture of 0.632 g (2.75 mmol) of (4,4-diethylthiochroman-6-yl)acetylene (Compound 27), 64 mg (0.33 mmol) of copper (I) iodide, and 5.08 g (50.3 mmol) of triethylamine were degassed with argon for 15 minutes. To the suspension was added 0.83 g (3.00 mmol) of ethyl 6-iodo-nicotinate (Compound 21) and then 0.15 g (0.22 mmol) of Bis(triphenylphosphine)palladium (II) chloride. The suspension was degassed with argon for an additional 5 minutes, the tube was sealed and the mixture stirred at 55° C. for 16 hours.

The mixture was cooled to room temperature and filtered through celite and silica gel using 200 mL of hexane and 20 mL of ethyl acetate. The solvents were removed in-vacuo and the residual oil was purified by flash chromatography (SiO$_2$, 5% ethyl acetate in hexanes) to give the title compound as a yellow oil.

PMR (CDCl$_3$): δ0.81 (6H, t, J=7.3 Hz), 1.43 (3H, t, J=6.8 Hz), 1.64 (2H, m), 1.79 (2H, m), 1.98 (2H, t, J=6.1 Hz), 3.04 (2H, t, J=6.3 Hz), 4.32 (2H, q, J=7.1 Hz), 7.10 (1H, dd, J=1.6 Hz), 7.46 (1H, d, J=1.6 Hz), 7.58 (1H, d, J=8.2 Hz), 8.27 (1H, dd, J=2.2, 8.2 Hz), 9.19 (1H, d, J=2.2 Hz).

Ethyl 4-[2-(4,4-diethylthiochroman-6-yl)-ethyn-1-yl)benzoate (Compound 1)

A mixture of 0.338 g (1.47 mmol) of (4,4-diethylthiochroman-6-yl)acetylene, 24 mg (0.13 mmol) of copper (I) iodide, and 2.54 g (25 mmol) of triethylamine were degassed with argon for 15 minutes. To the suspension was added 0.57 g (2.07 mmol) of ethyl 4-iodobenzoate (Compound 22) and then 0.12 g (0.17 mmol) of bis(triphenylphosphine)palladium (II) chloride. The suspension was degassed with argon for an additional 5 minutes, the tube was sealed and the mixture stirred at 55° C. for 16 hours.

The mixture was cooled to room temperature and filtered through celite and silica gel using 200 mL of hexane and 20 mL of ethyl acetate. The solvents were removed in-vacuo and residual oil purified by flash chromatography (SiO$_2$, 5% ethyl acetate in hexanes) to give the title compound as a yellow oil.

PMR (CDCl$_3$): δ0.82 (6H, t, J=7.4 Hz), 1.41 (3H, t, J=7.1 Hz), 1.65 (2H, m), 1.79 (2H, m). 1.98 (2H, t, J=6.1 Hz), 3.03 (2H, t, J=6.2 Hz), 4.38 (2H, q, J=7.1 Hz), 7.08 (1H, d, J=1.6, 8.2 Hz), 7.20 (1H, dd, J=1.67, 8.2 Hz), 7.37 (1H, s), 7.57 (1H, d, J=8.4 Hz), 8.01 (1H, d, J=8.4 Hz).

4-Propyl-6-(4-bromophenylthio)-4-hexanol (Compound 28)

To a stirred suspension of 14 g (57 mmol) of cerium trichloride in 40 mL of tetrahydrofuran was added 6.18 g of ethylmagnesium bromide (60 mmol, 2M in THF). The resulting mixture was stirred for 1 hour and cooled to 0° C. A solution of 4.91 g (17.0 mmol) of ethyl 3-(4-bromophenylthio)propionate (Compound 23) in 20 mL of tetrahydrofuran was then cannulated into the cool mixture and the resulting mixture stirred at room temperature for 16 hours. The reaction mixture was then cooled to 0° C. and treated with 200 mL of water and extracted with 5×50 mL of ether.

The ether extracts were combined and washed successively with 2×20 mL of saturated aqueous NaCl and dried (Na$_2$SO$_4$). The solvent was removed in-vacuo and the residue purified by flash chromatography (SiO$_2$; 10% ethyl acetate in hexanes) to give the title compound as a greenish oil.

PMR (CDCl$_3$): δ0.92 (6H, t, J=7.0 Hz), 1.29 (5H, m), 1.43 (4H, m) 1.75 (2H, m), 2.95 (2H, s), 7.20 (2H, dd, J=2.0, 6.5 Hz), 7.40 (2H, dd, J=2.1, 6.7 Hz).

6-Bromo-4,4-dipropylthiochroman (Compound 29)

A mixture of 1.13 g (7.92 mmol) of phosphorus pentoxide in 10 mL of methanesulfonic acid was heated for 45 minutes at 75° C. The solution was allowed to cool slightly and 3.25 g (9.85 mmol) of 4-propyl-6-(4 -bromophenylthio)-4-hexanol (Compound 28) was added. The reaction was stirred at room temperature for 2 hours. The mixture was then cooled to 0° C., treated with 50 mL of water and extracted with 3×50 mL of ether.

The ether extracts were combined and washed with saturated aqueous NaCl and then dried (Na$_2$SO$_4$). The solvent was removed in-vacuo and the residual oil purified by flash chromatography (SiO$_2$, 10% ethyl acetate in hexanes) to give the title compound as an orange oil.

PMR (CDCl$_3$): δ0.89 (6H, t, J=7.5 Hz), 1.20 (4H, m), 1.59 (4H, m), 1.97 (2H, m), 2.99 (2H, m), 6.96 (1H, d, J=8.3 Hz), 7.13 (1H, dd, J=2.1, 8.4 Hz), 7.30 (1H, s).

(4,4-Dipropylthiochroman-6-yl)(trimethylsilyl)acetylene (Compound 30)

A mixture of 2.04 g (6.54 mmol) of 6-bromo-4,4 -dipropylthiochroman (Compound 29), 0.12 g (0.64 mmol) of copper (I) iodide and 5.4 g (54 mmol) of triethylamine was degassed using argon for 15 minutes at −78° C. To the suspension was added 1.95 g (19.8 mmol) of (trimethylsilyl)acetylene then 0.41 g (58 mmol) of bis(triphenylphosphine)palladium (II) chloride. The solution was degassed with argon for an additional 5 minutes and the resulting mixture was allowed to warm to 0° C. The tube was sealed and the mixture heated to 55° C. for 15 hours.

The mixture was allowed to cool to room temperature and was filtered through celite and silica gel using 200 mL of hexane. The solvent was removed in-vacuo and the residual oil purified by flash chromatography (SiO$_2$, 100% hexane) to give the title compound as an orange oil.

PMR (CDCl$_3$): δ0.23 (9H, s), 0.86 (6H, t, J=7.4 Hz), 1.17 (5H, m), 1.58 (4H, m), 1.95 (2H, m), 2.98 (2H, m), 6.96 (1H, d, H=8.1 Hz), 7.09 (1H, dd, J=1.7, 8.1 Hz), 7.26 (1H, d, J=1.7 Hz).

(4,4-Dipropylthiochroman-6-yl)acetylene (Compound 31)

A solution of 1.82 g (32.4 mmol) of potassium hydroxide in 1.8 mL of water and 10.0 mL of ethanol was added to 1.22 g (3.70 mmol) of (4,4-dipropylthiochroman-6-yl)(trimethylsilyl)acetylene (Compound 30) and the resulting mixture stirred at room temperature for 5 hours during which time it became homogeneous. The solvent was removed in-vacuo and the residue was acidified with 5% aq H$_2$SO$_4$ and the product was extracted with 2×50 mL of ether.

The combined ether extracts were washed successively with 10% aqueous NaHCO$_3$ and saturated aqueous NaCl. The solvent was removed in-vacuo and the residue purified by Kugelrohr distillation (135° C., 0.75 mm) to give the title compound as a yellow oil.

PMR (CDCl$_3$): δ0.88 (6H, t, J=7.3 Hz), 1.20 (4H, m), 1.59 (4H, m), 1.98 (2H, m), 3.01 (3H, overlapping m, s), 7.02 (1H, d, J=8.1 Hz), 7.13 (1H, dd, J=1.8, 8.1 Hz), 7.32 (1H, d, J=1.7 Hz).

Ethyl 2-[2-(4,4-dipropylthiochroman-6-yl)-ethyn-1-yl]-5 -nicotinate (Compound 7)

A mixture of 0.760 g (2.95 mmol) of (4,4 -dipropylthiochroman-6-yl)acetylene, (Compound 31), 61 mg (0.32 mmol) of copper (I) iodide, and 3.6 g (3 mmol) of triethylamine were degassed with argon for 15 minutes. To the suspension was added 0.89 g (3.22 mmol) of ethyl-6-iodonicotinate (Compound 21) and then 0.30 g (0.43 mmol) of bis(triphenylphosphine)palladium (II) chloride. The suspension was degassed with argon for an additional 5 minutes, the tube was sealed and the mixture stirred at 55° C. for 16 hours and at room temperature for six days.

The mixture was then filtered through celite and silica gel using 200 mL of hexane and 20 mL of ethyl acetate. The solvents were removed in-vacuo and residual oil purified by flash chromatography (SiO$_2$, 5% ethyl acetate in hexanes) to give the title compound as an orange oil.

PMR (CDCl$_3$): δ0.89 (6H, t, J=7.3 Hz), 1.23 (4H, m), 1.43 (3H, t, J=7.1 Hz), 1.62 (4H, m), 2.00 (2H, m), 3.03 (2H, m), 4.42 (2H, q, J=7.1 Hz), 7.09 (1H, d, J=8.1 Hz), 7.25 (1H, dd, J=1.7, 8.5 Hz), 7.46 (1H, d, J=1.7 Hz), 7.57 (1H, dd, J=0.8, 8.2 Hz), 8.27 (1H, dd, J=2.2, 8.2 Hz), 9.19 (1H, d, J=2.1 Hz).

Ethyl 4-(2-(4,4-dipropylthiochroman-6-yl)-ethyn-1 -yl]benzoate (Compound 5)

A mixture of 0.338 g (1.47 mmol) of 4,4 -dipropylthiochroman-6-yl)acetylene (Compound 31), 24 mg, (0.13 mmol) of copper (I) iodide, and 2.54 g (25 mmol of triethylamine were degassed with argon for 15 minutes. To the suspension was added 0.57 g (2.07 mmol) of ethyl 4-iodobenzoate (Compound 22) and then 0.12 g (0.17 mmol) of bis(triphenylphosphine)palladium (II) chloride. The suspension was degassed with argon for an additional 5 minutes, the tube was sealed and the mixture stirred at 55° C. for 16 hours.

The mixture was cooled to room temperature and filtered through celite and silica gel using 200 mL of hexane and 20 mL of ethyl acetate. The solvents were removed in-vacuo and residual oil purified by flash chromatography (SiO$_2$, 5% ethyl acetate in hexanes) to give the title compound as a yellow oil.

PMR (CDCl$_3$): δ0.89 (6H, t, J=7.3 Hz), 1.22 (4H, m), 1.40 (3H, t, J=7.2 Hz), 1.55 (2H, m), 1.68 (2H, m), 1.98 (2H, m), 3.01 (2H, m), 4.37 (2H, q, J=7.1 Hz), 7.06 (1H, d, J=8.2 Hz), 7.18 (1H, dd, J=1.7, 8.1 Hz), 7.36 (1H, d, J=1.7 Hz), 7.58 (2H, d, J=8.7 Hz), 8.01 (2H, d, J=8.1 Hz).

5-Butyl-7-(4-bromophenylthio)-5-heptanol (Compound 32)

To a stirred suspension of 9.5 g (39 mmol) of cerium trichloride in 30 mL of tetrahydrofuran was added 5.9 g of butylmagnesium bromide (50 mmol, 2M in THF). The resulting mixture was stirred for 1 hour at room temperature and then cooled to 0° C. A solution of 4.29 g (14.8 mmol) of ethyl 3-(4-bromophenylthio)propionate (Compound 23) in 15 mL of tetrahydrofuran was then cannulated into the cool mixture and the resulting suspension stirred at room temperature for 12 hours. The reaction mixture was then recooled to 0° C. and treated with 200 mL of water and extracted with 5×50 mL of ether.

The ether extracts were combined and washed successively with 2×20 mL of saturated aqueous NaCl and dried (Na$_2$SO$_4$). The solvent was removed in-vacuo and the residue purified by flash chromatography (SiO$_2$, 10% ethyl acetate in hexanes) to give the title compound as an orange oil.

PMR (CDCl$_3$): δ0.91 (6H, t, J=7.2 Hz), 1.26 (8H, m), 1.43 (4H, m), 1.75 (2H, m), 2.97 (2H, m), 7.20 (2H, d, J=1.9 Hz), 7.41 (2H, d, J=1.9 Hz).

6-Bromo-4,4-dibutylthiochroman (Compound 33)

A mixture of 0.87 g (6.1 mmol) of phosphorus pentoxide in 8 mL of methanesulfonic acid was heated for 45 minutes at 75° C. The solution was allowed to cool slightly and 3.59 g (10.0 mmol) of 5-butyl-7-(4-bromophenylthio)-5-heptanol (Compound 32) was added. The resulting mixture was stirred at room temperature for 2 hours. The mixture was then cooled to 0° C. and treated with 50 mL of water and extracted with 3×40 mL of ether.

The ether extracts were combined and washed with saturated aqueous NaCl and then dried (Na$_2$SO$_4$). The solvent was removed in-vacuo and the residual oil purified by flash chromatography (SiO$_2$, 5% ethyl acetate in hexanes) to give the title compound as an orange oil.

PMR (CDCl$_3$): δ0.88 (6H, t, J=7.3 Hz), 1.22 (8H, m), 1.66 (4H, m), 1.97 (2H, m), 2.98 (2H, m), 6.96 (1H, d, J=8.7 Hz), 7.13 (1H, dd, J=2.0, 8.3 Hz), 7.31 (1H, d, J=2.1 Hz).

(4,4-Dibutylthiochroman-6-yl)(trimethylsilyl)acetylene (Compound 34)

A mixture of 1.68 g (5.38 mmol) of 6-bromo-4,4-dibutylthiochroman (Compound 33), 0.28 g (1.5 mmol) of copper (I) iodide and 2.5 g (25 mmol) of triethylamine was degassed with argon for 15 minutes at −78° C. To the suspension was added 1.18 g (71 mmol) of (trimethylsilyl)acetylene and 0.24 g (0.35 mmol) of bis(triphenylphosphine)palladium (II) chloride. The solution was degassed with argon for an additional 5 minutes and the resulting mixture was allowed to warm to 0° C. The tube was sealed and the mixture was heated to 55° C. for 22 hours.

The mixture was allowed to cool to room temperature and was filtered through celite and silica gel using 200 mL of hexane. The solvent was removed in-vacuo and the residual oil purified by flash chromatography (SiO$_2$, 100% hexane) to give the title compound as an orange oil.

PMR (CDCl$_3$): δ0.25 (9H, s), 0.88 (6H, t, J=7.3 Hz), 1.25 (8H, m), 1.65 (4H, m), 1.98 (2H, m), 3.00 (2H, m), 7.05 (1H, d, H=8.1 Hz), 7.11 (1H, dd J=1.7, 8.8 Hz), 7.29 (1H, d, J=1.7 Hz).

(4,4-Dibutylthiochroman-6-yl)acetylene (Compound 35)

A solution of 1.41 g (25 mmol) of potassium hydroxide in 1.4 mL of water and 10.0 mL of ethanol was added to 1.44 g (4.00 mmol) of (4,4-dibutylthiochroman-6-yl)(trimethylsilyl)acetylene (Compound 34) and the resulting mixture stirred at room temperature for 16 hours during which time it became homogeneous. The solvent was removed in-vacuo and the residue was acidified with 5% aqueous H$_2$SO$_4$. The product was extracted with 2×50 mL of ether.

The combined ether extracts were washed successively with 10% aqueous NaHCO$_3$ and saturated aqueous NaCl. The solvent was removed in-vacuo and the residue purified by Kugelrohr distillation (165° C., 3 mm) to give the title compound as an orange oil.

PMR (CDCl$_3$): δ0.88 (6H, t, J=7.3 Hz), 1.22 (8H, m), 1.66 (4H, m), 1.97 (2H, m), 3.00 (3H, overlapping m, s), 7.02 (1H, d, J=8.1 Hz), 7.13 (1H, dd, J=1.8, 8.1 Hz), 7.32 (1H, d, J=1.7 Hz).

Ethyl 2-[2-(4,4-dibutylthiochroman-6-yl)-ethyn-1-yl]-5-nicotinate (Compound 11)

A mixture of 0.49 g (1.72 mmol) of (4,4-dibutylthiochroman-6-yl)acetylene (Compound 35), 52 mg (0.27 mmol) of copper (I) iodide, 2.20 g (22 mmol) of triethylamine and 0.49 g (1.75 mmol) of ethyl 6-iodonicotinate (Compound 21) was degassed with argon for 10 minutes. To the suspension was added 0.10 g (0.15 mmol) of bis(triphenylphosphine)palladium (II) chloride. The suspension was degassed with argon for an additional 5 minutes, the tube was sealed, and the mixture stirred at 55° C. for 8 hours and at room temperature for 24 hours.

The mixture was cooled to room temperature and filtered through celite and silica gel using 200 mL of hexane. The solvents were removed in-vacuo and the residual oil purified by flash chromatography (SiO$_2$, 5% ethyl acetate in hexanes) to give the title compound as an orange oil.

PMR (CDCl$_3$): δ0.88 (6H, t, J=7.2 Hz), 1.25 (8H, m), 1.43 (3H, t, J=7.1 Hz), 1.64 (4H, m), 2.00 (2H, m), 3.03 (2H, m), 4.42 (2H, q, J=7.1 Hz), 7.09 (1H, d, J=8.2 Hz), 7.26 (1H, dd, J=1.7, 7.8 Hz), 7.47 (1H, d, J=1.7 Hz), 7.58 (1H, d, J=8.3 Hz), 8.27 (1H, dd, J=2.2, 8.3 Hz), 9.20 (1H, d, J=3.3 Hz)

Ethyl 4-[2-(4,4-dibutylthiochroman-6-yl)-ethyn-1-yl]benzoate (Compound 9)

A mixture of 0.234 g (0.82 mmol) of (4,4-dibutylthiochroman-6-yl)acetylene (Compound 35), 21 mg (0.11 mmol) of copper (I) iodide, and 1.45 g (14 mmol) of triethylamine were degassed with argon for 15 min. To the suspension was added 0.49 g (1.8 mmol) of ethyl 4-iodobenzoate (Compound 21) and then 0.065 g (0.09 mmol) of bis(triphenyliphosphine)palladium (II) chloride. The suspension was degassed with argon for an additional 5 minutes, the tube was sealed and the mixture stirred at 55° C. for 20 hours.

The mixture was cooled to room temperature and filtered through celite and silica gel using 200 mL of hexane and 20 mL of ethyl acetate. The solvents were removed in-vacuo and the residual oil purified by flash chromatography (SiO$_2$, 5% ethyl acetate in hexanes) to give the title compound as a yellow oil.

PMR (CDCl$_3$): δ0.89 (6H, t, J=7.3 Hz), 1.24 (8H, m), 1.41 (3H, t, J=7.2 Hz), 1.60 (2H, m), 1.72 (2H, m), 2.00 (2H, m), 3.02 (2H, m), 4.38 (2H, q, J=7.2 Hz), 7.07 (1H, d, J=8.1 Hz), 7.19 (1H, dd, J=1.7, 8.1 Hz), 7.36 (1H, d, J=1.7 Hz), 7.58 (1H, d, J=8.4 Hz), 8.02 (1H, d, J=8.4 Hz).

[2-(4,4-diethylthiochroman-6-yl)-ethyn-1-yl]-5-nicotinic acid (Compound 4)

A solution of 1.15 g (20.5 mmol) of potassium hydroxide in 1.0 mL of water and 10.0 mL of ethanol was added to 0.456 g (1.20 mmol) of ethyl 2-[2-(4,4-diethylthiochroman-6-yl)-ethyn-1-yl]-5-nicotinate (Compound 3) and the resulting mixture was stirred at room temperature for 16 hours during which it became homogeneous. The solvent was removed in-vacuo and the residue was acidified with 5% aqueous H$_2$SO$_4$. The product was extracted with 2×65 mL of 15% ether in methylene chloride.

The combined ether extracts were washed successively with 10% aqueous NaHCO$_3$, saturated aqueous Nacl, and dried over Na$_2$SO$_4$. The solvent was removed in-vacuo yielding a yellow solid which was recrystallized using EtOH to give the title compound as a yellow solid.

PMR (DMSO): δ0.70 (6H, t, J=7.5 Hz), 1.54 (2H, m), 1.73 (2H, m), 1.86 (2H, m), 3.01 (2H, m), 7.11 (1H, d, J=8.1 Hz), 7.26 (1H, dd, J=1.7, 8.3 Hz), 7.44 (1H, d, J=1.5 Hz), 7.73 (1H, d, J=8.2 Hz), 8.25 (1H, dd, J=2.2, 8.1 Hz), 9.04 (1H, d, J=1.3 Hz).

4-[2-(4,4-dipropylthiochroman-6-yl)-ethyn-1-yl]benzoic acid (Compound 6)

A solution of 1.15 g (20.5 mmol) of potassium hydroxide in 1.0 mL of water and 10.0 mL of ethanol was added to 0.381 g (0.94 mmol) of ethyl 4-[2-(4,4 -dipropylthiochroman-6-yl)-ethyn-1-yl]benzoate (Compound 5) and the resulting mixture stirred at room temperature for 15 hours during which time it became homogeneous. The solvent was removed in-vacuo and the residue was acidified with 5% aqueous $H_2SO_4$. The product was extracted with 2×65 mL of 15% ether in methylene chloride.

The combined ether extracts were washed successively with 10% aqueous $NaHCO_3$, saturated aqueous NaCl, and dried over $Na_2SO_4$. The solvent was removed in-vacuo yielding a yellow solid which was recrystallized using EtOH to give the title compound as a yellow solid.

PMR (DMSO): δ0.82 (6H, t, J=7.4 Hz), 1.13 (5H, m), 1.51 (2H, m), 1.67 (2H, m), 1.92 (2H, m), 3.01 (2H, m), 7.08 (1H, d, J=8.1 Hz), 7.20 (1H, dd, J=1.7, 8.1 Hz), 7.40 (1H, d, J=1.66 Hz), 7.53 (1H, d, J=8.3 Hz), 7.91 (1H, d, J=8.3 Hz).

2-[2-(4,4-dipropylthiochroman-6-yl)-ethyn-1-yl]-5-nicotinic acid (Compound 8)

A solution of 1.08 g (19.3 mmol) of potassium hydroxide in 1.0 mL of water and 10.0 mL of ethanol was added to 0.470 g (1.15 mmol) of ethyl 2-[2-(4,4 -dipropylthiochroman-6-yl)-ethyn-1-yl]-5-nicotinoate (Compound 7) and the resulting mixture stirred at room temperature for 15 hours during which time it became homogeneous. The solvent was removed in-vacuo and the residue was acidified with 5% aqueous $H_2SO_4$. The product was extracted with 2×65 mL of 15% ether in methylene chloride.

The combined ether extracts were washed successively with 10% aqueous $NaHCO_3$, saturated aqueous NaCl, and dried over $Na_2SO_4$. The solvent was removed in-vacuo yielding a yellow solid which was recrystallized using EtOH to give the title compound as a yellow solid.

PMR (DMSO): δ0.85 (6H, t, J=7.3 Hz), 1.14 (4H, m), 1.52 (2H, m), 1.70 (2H, m), 1.93 (2H, m), 3.03 (2H, m), 3.32 (1H, s), 7.13 (1H, d, J=8.1 Hz), 7.27 (1H, dd, J=1.6, 8.1 Hz), 7.47 (1H, d, J=1.5 Hz), 7.75 (1H, d, J=8.3 Hz), 8.27 (1H, dd, J=2.2, 8.2 Hz), 9.20 (1H, d, J=2.1 Hz).

2-[2-(4,4-dibutylthiochroman-6-yl)-ethyn-1-yl]-5 -nicotinic acid (Compound 12)

A solution of 1.05 g (18.8 mmol) of potassium hydroxide in 1.0 mL of water and 10.0 mL of ethanol was added to 0.341 g (0.78 mmol) of ethyl 2-[2-(4,4 -dibutylthiochroman-6-yl)-ethyn-1-yl]-5-nicotinoate (Compound 11) and the resulting mixture stirred at room temperature for 15 hours during which time it became homogeneous. The solvent was removed in-vacuo and the residue was acidified with 5% aqueous $H_2SO_4$. The product was extracted with 2×65 mL of 15% ether in methylene chloride.

The combined ether extracts were washed successively with 10% aqueous $NaHCO_3$, saturated aqueous NaCl, and dried over $Na_2SO_4$. The solvent was removed in-vacuo yielding a yellow solid which was recrystallized using EtOH to give the title compound as a yellow solid.

PMR (DMSO): δ0.83 (6H, t, J=7.3 Hz), 1.09 (4H, m), 1.23 (4H, m), 1.54 (2H, m), 1.72 (2H, m), 1.92 (2H, m), 3.02 (2H, m), 3.32 (1H, m), 7.12 (1H, d, J=8.1 Hz), 7.27 (1H, dd, J=1.7, 8.2 Hz), 7.47 (1H, d, J=1.7 Hz), 7.74 (1H, dd, J=0.8, 8.3 Hz), 8.26 (1H, dd, J=2.2, 8.2 Hz), 9.04 (1H, dd, J=0.8, 2.2 Hz).

Using as an example the method for the preparation of Compound 1, but substituting the appropriately substituted ethynylthiochroman (Formula 12 in Reaction Scheme 1) and the appropriate halo substituted phenyl ester (Formula 3, prepared for example as specifically described for Compound 22) the following further examplary compounds of the invention can be prepared:

ethyl 4-[(4,4-diethyl-7-methylthiochroman-6-yl)ethynyl] benzoate;

ethyl 4-[(4,4,7-tri-ethylthiochroman-6-yl)ethynyl] benzoate;

ethyl 4-[(4,4-diethyl-7-propylthiochroman-6-yl)ethynyl] benzoate;

ethyl 4-[(4,4-diethyl-7-hexylthiochroman-6-yl)ethynyl] benzoate;

ethyl 2-[4-[(4,4-diethylthiochroman-6-yl)ethynyl)phenyl] acetate;

ethyl 2-[[4-(4,4-diethyl-7-methylthiochroman-6 -yl)ethynyl)-phenyl]acetate;

ethyl 2-[4-(4,4,7-triethylthiochroman-6-yl)ethynyl)phenyl]acetate;

ethyl 2-[4-(4,4-diethyl-7-hexylthiochroman-6 -yl)ethynyl)phenyl]acetate;

ethyl 3-[4-(4,4-diethylthiochroman-2-yl)ethynyl)phenyl] propionate;

ethyl 3-[4-(4,4-diethyl-7-methylthiochroman-6-yl)ethynyl)phenyl]propionate;

ethyl 3-[4-(4,4-triethylthiochroman-6-yl)ethynyl)phenyl] propionate;

ethyl 3-[4-(4,4-diethyl-7-hexylthiochroman-6-yl)ethynyl)phenyl]propionate;

ethyl 5-[4-(4,4-diethylthiochroman-6-yl)ethynyl)phenyl] pentanoate;

ethyl 5-[4-(4,4-diethyl-7-methylthiochroman-6-yl)ethynyl)phenyl]pentanoate;

ethyl 5-[4-(4,4,7-triethylthiochroman-6-yl)ethynyl)phenyl]pentanoate, and the corresponding free carboxylic acid derivatives.

Using the following examplary intermediates of Formula 18 in Reaction Scheme 2 or 3, 4,4,7-triethyl-6-ethynyl-chroman;

4,4-diethyl-6-ethynyl-7-propylchroman;

4,4-diethyl-6-ethynyl-7-butylchroman;

4,4-diethyl-6-ethynyl-7-pentylchroman;

4,4-diethyl-6-ethynyl-7-hexylchroman;

the following examplary compounds of the invention can be prepared:

ethyl 4-[(4,4,7-triethylchroman-6-yl)ethynyl]benzoate;

ethyl 4-[(4,4-diethyl-7-propylchroman-6-yl)ethynyl]benzoate;

ethyl 4-[(4,4-diethyl-7-hexylchroman-6-yl)ethynyl]benzoate;

ethyl [2-(4-(4,4-diethylchroman-6-yl)ethynyl)phenyl]acetate;

ethyl [2-(4-(4,4-diethyl-7-methylchroman-6 -yl)ethynyl)-phenyl]acetate;

ethyl [2-(4-(4,4,7-triethylchroman-6-yl)ethynyl)phenyl] acetate;

ethyl [2-(4-(4,4-diethyl-7-hexylchroman-6-yl)ethynyl)phenyl]acetate;

ethyl 3-[4-(4,4-diethylchroman-2-yl)ethynyl)phenyl]propionate;

ethyl 3-[4-(4,4-diethyl-7-methylchroman-6-yl)ethynyl)-phenyl] propionate;

ethyl 3-[4-(4,4,7-triethylchroman-6-yl)ethynyl)phenyl] propionate;

ethyl 3-[4-(4,4-diethyl-7-hexylchroman-6-yl)ethynyl)phenylpropionate;

ethyl 5-[4-(4,4-diethylchroman-6-yl)ethynyl)phenyl]pentanoate;

ethyl 5-[4-(4,4-diethyl-7-methylchroman-6-yl)ethynyl)phenyl]pentanoate;

ethyl 5-[4-(4,4,7-triethylchroman-6-yl)ethynyl)phenyl] pentanoate, and the corresponding fee carboxylic acid derivatives.

The positional isomers of the above-noted examples (and of analogous compounds) can also be prepared in accordance with the foregoing procedures or by apparent modifications of such procedures.

Still further, substituting the appropriate 6-ethynylthiochroman or-6-ethynylchroman of Formula 12 and 18, respectively, and reacting them with the appropriate halogenated heteroaromatic compound as per Reaction Schemes 1 and 2, the following further examplary compounds of the invention can be prepared.

ethyl 6-[(4,4-diethyl-7-methylthiochroman-6-yl)ethynyl] nicotinate;

ethyl 6-[(4,4,7-triethylthiochroman-6-yl)ethynyl]nicotinate;

ethyl 6-[(4,4-diethyl-7-propylthiochroman-6-yl)ethynyl] nicotinate;

ethyl 6-[(4,4-diethyl-7-hexylthiochroman-6-yl)ethynyl] nicotinate;

ethyl [(4,4-diethylthiochroman-6-yl)ethynyl)-pyrid-5-yl] acetate;

ethyl [((4,4-diethyl-7-methylthiochroman-6 -yl)ethynyl)-pyrid-5-yl]acetate;

ethyl [((4,4,7-triethylthiochroman-6-yl)ethynyl)pyrid-5-yl]acetate;

ethyl [((4,4-diethyl-7-hexylthiochroman-6-yl)ethynyl)pyrid-5-yl]acetate;

ethyl 3-[((4,4-diethylthiochroman-2-yl)ethynyl)pyrid-5-yl]propionate;

ethyl 3-[((4,4-diethyl-7-methylthiochroman-6-yl)ethynyl)pyrid-5-yl]propionate;

ethyl 3-[((4,4,7-triethylthiochroman-6-yl)ethynyl)pyrid-5-yl]propionate;

ethyl 3-[(4,4-diethyl-7-hexylthiochroman-6-yl)ethynyl)pyrid-5-yl]propionate;

ethyl 5-[((4,4-diethylthiochroman-6-yl)ethynyl)pyrid-5-yl]pentanoate;

ethyl 5-[((4,4-diethyl-7-methylthiochroman-6-yl)ethynyl)pyrid-5-yl]pentanoate;

ethyl 5-[((4,4,7-triethylthiochroman-6-yl)ethynyl)pyrid-5-yl]pentanoate;

ethyl 5-((4,4-diethylthiochroman-6-yl)ethynyl)fur-2-yl] acetate;

ethyl [5-((4,4-diethyl-7-methylthiochroman-6 -yl)ethynyl)-fur-2-yl]acetate;

ethyl [5-((4,4,7-triethylthiochroman-6-yl)ethynyl)fur-2-yl]acetate;

ethyl [5-((4,4-diethyl-7-hexylthiochroman-6-yl)ethynyl)fur-2-yl]acetate;

ethyl 5-[((4,4-diethylthiochroman-6-yl)ethynyl)fur-2-yl] pentanoate;

ethyl 5-[5((4,4-diethyl-7-methylthiochroman-6-yl)ethynyl)fur- 2-yl]pentanoate;

ethyl 5-[5-((4,4,7-triethylthiochroman-6-yl)ethynyl)fur-2-yl]pentanoate;

ethyl 5-[5-((4,4-dietyl-7-hexylthiochroman-6-yl)ethynyl)fur- 2-yl]pentanoate;

ethyl [5-((4,4-diethylthiochroman-6-yl)ethynyl)thien-2-yl]acetate;

ethyl [5-((4,4-diethyl-7-methylthiochroman-6-yl)ethynyl)-thien- 2-yl]acetate;

ethyl [5-((4,4,7-triethylthiochroman-6-yl)ethynyl)thien-2-yl]acetate;

ethyl [5-((4,4-diethyl-7-hexylthiochroman-6-yl)ethynyl)thien- 2-yl]acetate;

ethyl 5-[5-4,4-diethylthiochroman-6-yl)-ethynyl)thien-2-yl]pentanoate;

ethyl 5-[5-((4,4-diethyl-7-methylthiochroman-6 -yl)-ethynyl)thien-2-yl]pentanoate;

ethyl 5-[5-((4,4,7-triethylthiochroman-6-yl)ethynyl)thien- 2-yl]pentanoate;

ethyl 5-[5-((4,4-diethyl-7-hexylthiochroman-6-yl)ethynyl)thien- 2-yl]pentanoate;

ethyl [6-((4,4-diethylthiochroman-6-yl)ethynyl)pyridazin- 3-yl]acetate;

ethyl [6((4,4-diethyl-7-methylthiochroman-6 -yl)ethynyl)-pyridazin-3-yl]acetate;

ethyl [6-((4,4,7-triethylthiochroman-6-yl)ethynyl)pyridazin- 3-yl]acetate;

ethyl [6-((4,4-diethyl-7-hexylthiochroman-6-yl)ethynyl)pyridazin-3-yl]acetate;

ethyl-5-[6((4,4-diethylthiochroman-6-yl)ethynyl)pyridazin- 3-yl]pentanoate;

ethyl 5-[6-((4,4-diethyl-7-methylthiochroman-6 -yl)-ethynyl)pyridazin-3-yl]pentanoate;

ethyl 5-[6-((4,4,7-triethylthiochroman-6-yl)ethynyl)pyridazin- 3-yl]pentanoate;

ethyl 5-[6-((4,4-diethyl-7-hexylthiochroman-6-yl)ethynyl)pyridazin- 3-yl]pentanoate;

ethyl [5-((4,4-diethylthiochroman-6-yl)ethynyl)pyrimidin- 2-yl]acetate;

ethyl [5-((4,4-diethyl-7-methylthiochroman-6 -yl)ethynyl)-pyrimidin-2-yl]acetate;

ethyl [5-((4,4,7-triethylthiochroman-6-yl)ethynyl)pyrimidin- 2-yl]acetate;

ethyl [5-((4,4-diethyl-7-hexylthiochroman-6-yl)ethynyl)pyrimidin- 2-yl]acetate;

ethyl 5-[5-(4,4-diethylthiochroman-6-yl)ethynyl)pyrimidin- 2-yl]pentanoate;

ethyl 5-[5-((4,4-diethyl-7-methylthiochroman-6 -yl)-ethynyl)pyrimidin-2-yl]pentanoate;

ethyl 5-[5-((2,2,4,4,7-triethylthiochroman-6-yl)ethynyl)pyrimidin- 2-yl]pentanoate;

ethyl 5-[5-((4,4-diethyl-7-hexylthiochroman-6-yl)ethynyl)pyrimidin- 2-yl]pentanoate;

ethyl [5-((4,4-diethylthiochroman-6-yl)ethynyl)pyrazin-2-yl]acetate;

ethyl [5-((4,4-diethyl-7-methylthiochroman-6 -yl)ethynyl)-pyrazin-2-yl]acetate;

ethyl [5-((2,2,7-triethylthiochroman-6-yl)ethynyl)pyrazin- 2-yl]acetate;

ethyl [5-((4,4-diethyl-7-hexylthiochroman-6-yl)ethynyl)pyrazin-2-yl]acetate;

ethyl 5-[5-((4,4-diethylthiochroman-6-yl)ethynyl)pyrazin-2-yl]pentanoate;

ethyl 5-[5-((4,4-diethyl-7-methylthiochroman-6-yl)ethynyl)pyrazin-2-yl]pentanoate;

ethyl 5-[5-((4,4,7-triethylthiochroman-6-yl)ethynyl)pyrazin-2-yl]pentanoate;

ethyl 5-[5-((4,4-diethyl-7-hexylthiochroman-6-yl)ethynyl)pyrazin-2-yl]pentanoate;

ethyl 6-[4,4-diethylchroman-6-yl)ethynyl]nicotinate;

ethyl 6-[(4,4-diethyl-7-hexylchroman-6-yl)ethynyl]nicotinate;

ethyl [2-((4,4-diethylchroman-6-yl)ethynyl)pyrid-5-yl]acetate;

ethyl [2-((4,4-diethyl-7-methylchroman-6-yl)ethynyl)pyrid-5-yl]acetate;

ethyl [2-((4,4,7-triethylchroman-6-yl)ethynyl)pyrid-5-yl]acetate;

ethyl [2-((4,4-diethyl-7-hexylchroman-6-yl)ethynyl)pyrid-5-yl]acetate;

ethyl 3-[2-((4,4-diethylchroman-2-yl)ethynyl)pyrid-5-yl]propionate;

ethyl 3-[2-((4,4-diethyl-7-methylchroman-6-yl)ethynyl)pyrid-5-yl]propionate;

ethyl 3-[2((4,4,7-triethylchroman-6-yl)ethynyl)pyrid-5-yl]propionate;

ethyl 3-[2((4,4-diethyl-7-hexylchroman-6-yl)ethynyl)pyrid-5-yl]propionate;

ethyl 5-[2-((4,4-diethylchroman-6-yl)ethynyl)pyrid-5-yl]pentanoate;

ethyl 5-[2-((4,4-diethyl-7-methylchroman-6-yl)ethynyl)pyrid-5-yl]pentanoate;

ethyl 5-[2-((4,4,7-triethylchroman-6-yl)ethynyl)pyrid-5-yl]pentanoate;

ethyl 5-[2-((4,4-diethylchroman-6-yl)ethynyl)-fur-2-yl]acetate;

ethyl [5-((4,4-diethyl-7-methylchroman-6-yl)ethynyl)fur-2-yl]acetate;

ethyl [5-((4,4,7-triethylchroman-6-yl)-ethynyl)fur-2-yl]acetate;

ethyl [5-((4,4-diethyl-7-hexylchroman-6-yl)ethynyl-fur-2-yl]acetate;

ethyl 5-[5-((4,4-diethylchroman-6-yl)ethynyl)-fur-2-yl]pentanoate;

ethyl 5-[5-((4,4,7-pentamethylchroman-6-yl)ethynyl)fur-2-yl]pentanoate;

ethyl 5-[5-((4,4,7-triethylchroman-6-yl)ethynyl)fur-2-yl]pentanoate;

ethyl 5-[5-((4,4-diethyl-7-hexylchroman-6-yl)ethynyl)fur-2-yl]pentanoate;

ethyl 5-[5-((4,4-diethylchroman-6-yl)ethynyl)thien-2-yl]acetate;

ethyl [-((4,4-diethyl-7-methylchroman-6-yl)ethynyl)thien-2-yl]acetate;

ethyl [5-((4,4,7-triethylchroman-6-yl)ethynyl)thien-2-yl]acetate;

ethyl [5-((4,4-diethyl-7-hexylchroman-6-yl)ethynyl)thien-2-yl]acetate;

ethyl 5-[5((4,4-diethylchroman-6-yl)ethynyl)-thien-2-yl]pentanoate;

ethyl 5-[5-((4,4-diethyl-7-methylchroman-6-yl)ethynyl)thien-2-yl]pentanoate;

ethyl 5-[5-((4,4,7-triethylchroman-6-yl)ethynyl)thien-2-yl]pentanoate;

ethyl 5-[5-((4,4-diethyl-7-hexylchroman-6-yl)ethynyl)thien-2-yl]pentanoate;

ethyl [6-((4,4-diethylchroman-6-yl)ethynyl)pyridazin-3-yl]acetate;

ethyl [6-((4,4-diethyl-7-methylchroman-6-yl)ethynyl)pyridazin-3-yl]acetate;

ethyl [6-((4,4,7-triethylchroman-6-yl)ethynyl)pyridazin-3-yl]acetate;

ethyl [6-((4,4-diethyl-7-hexylchroman-6-yl)ethynyl)pyridazin-3-yl]acetate;

ethyl 5-[6-((4,4-diethylchroman-6-yl)ethynyl)pyridazin-3-yl]pentanoate;

ethyl 5-[6-((4,4-diethyl-7-methylchroman-6-yl)ethynyl)pyridazin-3-yl]pentanoate;

ethyl 5-[6-((4,4,7-triethylchroman-6-yl)ethynyl)pyridazin-3-yl]pentanoate;

ethyl 5-[6-((4,4-diethyl-7-hexylchroman-6-yl)ethynyl)pyradazin-3-yl]pentanoate;

ethyl [5-((4,4-diethylchroman-6-yl)ethynyl)pyrimidin-2-yl]acetate;

ethyl [5-((4,4-diethyl-7-methylchroman-6-yl)ethynyl)pyrimidin-2-yl]acetate;

ethyl [5-((4,4,7-triethylchroman-6-yl)ethynyl)pyrimidin-2-yl]acetate;

ethyl [5-((4,4-diethyl-7-hexylchroman-6-yl)ethynyl)pyrimidin-2-yl]acetate;

ethyl 5-[5-((4,4-diethylchroman-6-yl)ethynyl)pyrimidin-2-yl]pentanoate;

ethyl 5-[5-((4,4-diethyl-7-methylchroman-6-yl)ethynyl)pyrimidin-2-yl]pentanoate;

ethyl 5-[4-((4,4,7-triethylchroman-6-yl)ethynyl)pyrimidin-2-yl]pentanoate;

ethyl 5-[5-((4,4-diethyl-7-hexylchroman-6-yl)ethynyl)pyrimidin-2-yl]pentanoate;

ethyl [5-((4,4-diethylchroman-6-yl)ethynyl)pyrazin-2-yl]acetate;

ethyl [5-((4,4-diethyl-7-methylchroman-6-yl)ethynyl)pyrazin-2-yl]acetate;

ethyl [5-((4,4,7-triethylchroman-6-yl)ethynyl)pyrazin-2-yl]acetate;

ethyl [5-((4,4-diethyl-7-hexylchroman-6-yl)ethynyl)pyrazin-2-yl]acetate;

ethyl [5-[5-((4,4-diethylchroman-6-yl)ethynyl)pyrazin-2-yl]pentanoate;

ethyl 5-[5-((4,4-diethyl-7-methylchroman-6-yl)ethynyl)pyrazin-2-yl]pentanoate;

ethyl 5-[5-((4,4,7-triethylchroman-6-yl)ethynyl)pyrazin-2-yl]pentanoate;

ethyl 5-[5-((4,4-diethyl-7-hexylchroman-6-yl)ethynyl)pyrazin-2-yl]pentanoate, and the corresponding free carboxylic acids.

What is claimed is:

1. A compound of the formula

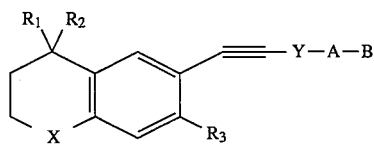

wherein $R_1$ and $R_2$, independently are n-alkyl groups having 2 to 8 carbons, or cyclo or branch-chained alkyl groups of 3 to 8 carbons;

$R_3$ is hydrogen or lower alkyl;

X is S, or O;

Y is a heteroaryl group selected from a group consisting of thienyl and furyl;

A is $(CH_2)_n$ where n is 0–5, lower branched chain alkyl having 3 to 6 carbons, cycloalkyl having 3 to 6 carbons, alkenyl having 2 to 6 carbons and 1 or 2 double bonds, alkynyl having 2 to 6 carbons and 1 or 2 triple bonds;

B is hydrogen, COOH or a pharmaceutically acceptable salt thereof, $COOR_5$, $CONR_6R_7$, —$CH_2OH$, $CH_2OR_8$, $CH_2OCOR_8$, CHO, $CH(OR_9)_2$, $CHOR_{10}O$, —$COR_{11}$, $CR_{11}(OR_9)_2$, or $CR_{11}OR_{10}O$, where $R_5$ is an alkyl group of 1 to 10 carbons, or a cycloalkyl group of 5 to 10 carbons, or $R_5$ is phenyl or lower alkylphenyl, $R_6$ and $R_7$ independently are hydrogen, an alkyl group of 1 to 10 carbons, or a cycloalkyl group of 5 to 10 carbons, or phenyl or lower alkylphenyl, $R_8$ is alkyl of 1 to 10 carbons, phenyl or lower alkylphenyl, $R_9$ is lower alkyl, $R_{10}$ is divalent alkyl radical of 2–5 carbons and $R_{11}$ is an alkyl, cycloalkyl or alkenyl group containing 1 to 5 carbons.

2. A compound in accordance with claim 1 where X is S.
3. A compound in accordance with claim 1 where X is O.
4. A compound in accordance with claim 1 where the $R_1$ and $R_2$ groups are identical with one another.
5. A compound in accordance with claim 1 where the $R_1$ and $R_2$ groups are both n-alkyl.
6. A compound in accordance with claim 1 where Y is thienyl.
7. A compound of the formula

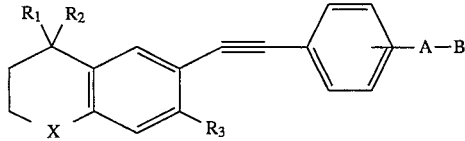

where $R_1$ and $R_2$, independently are n-alkyl groups having 2 to 8 carbons;

$R_3$ is hydrogen or lower alkyl;

X is S or O;

A is $(CH_2)_n$ where n is 0–5, and

B is hydrogen, COOH or a pharmaceutically acceptable salt thereof, $COOR_5$, $CONR_6R_7$, —$CH_2OH$, $CH_2OR_8$, $CH_2OCOR_8$, CHO, $CH(OR_9)_2$, $CHOR_{10}O$, —$COR_{11}$, $CR_{11}(OR_9)_2$, or $CR_{11}OR_{10}O$, where $R_5$ is an alkyl group of 1 to 10 carbons, or a cycloalkyl group of 5 to 10 carbons, or $R_5$ is phenyl or lower alkylphenyl, $R_6$ and $R_7$ independently are hydrogen, an alkyl group of 1 to 10 carbons, or a cycloalkyl group of 5 to 10 carbons, or phenyl or lower alkylphenyl, $R_8$ is alkyl of 1 to 10 carbons, phenyl or lower alkylphenyl, $R_9$ is lower alkyl, $R_{10}$ is divalent alkyl radical of 2–5 carbons and $R_{11}$ is an alkyl, cycloalkyl or alkenyl group containing 1 to 5 carbons.

8. A compound in accordance with claim 7 where X is S.
9. A compound in accordance with claim 8 where A is $(CH_2)_n$ and where n is O.
10. A compound in accordance with claim 9 where B is COOH, $COOR_5$, $CONR_6R_7$ or a pharmaceutically acceptable salt thereof.
11. A compound in accordance with claim 7 where X is O.
12. A compound in accordance with claim 11 where A is $(CH_2)_n$ and where n is O.
13. A compound in accordance with claim 12 where B is COOH, $COOR_5$, $CONR_6R_7$ or a pharmaceutically acceptable salt thereof.
14. A compound of the formula

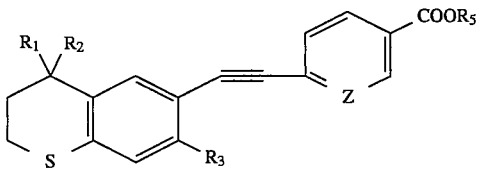

where where $R_1$ and $R_2$ are identical and are selected from the group consisting of ethyl, n-propyl and n-butyl;

Z is CH, and $R_5$ is ethyl or hydrogen.

15. A compound of claim 14 where $R_1$ and $R_2$ are ethyl.
16. A compound of claim 15 where Z is CH.
17. A compound of claim 14 where $R_1$ and $R_2$ are n-propyl.
18. A compound of claim 17 where Z is CH.
19. A compound of claim 14 where $R_1$ and $R_2$ are n-butyl.
20. A compound of claim 19 where Z is CH.

* * * * *

UNITED STATES PATENT AND TRADEMARK OFFICE
CERTIFICATE OF CORRECTION

PATENT NO. : 5,468,879  
DATED : November 21, 1995  
INVENTOR(S) : Chandraratna page 1 of 2

It is certified that error appears in the above-indentified patent and that said Letters Patent is hereby corrected as shown below:

Column 1, line 44, "substitituted" should be --substituted--;

Column 1, line 53, "compound" should be --compounds--;

Column 13, line 15, "CoI" should be --CuI--;

Column 16, between Formula 6 and 7, "LiAlH4" should be --$LiAlH_4$--;

Column 17, in Formula 3, "+L-Y-A-B" should be --+L-Y-A-B'--;

Column 17, line 49, "X=" should be --X--;

Column 18, line 31, "C°. C" should be --C°--;

Column 18, line 67, "4,4" should be --4.4--;

Column 19, line 19, "SiO2" should be --$SiO_2$--;

Column 27, line 6, "phenylpropionate" should be --phenyl]propionate--;

UNITED STATES PATENT AND TRADEMARK OFFICE
CERTIFICATE OF CORRECTION

PATENT NO. : 5,468,879
DATED : November 21, 1995
INVENTOR(S) : Chandraratna

It is certified that error appears in the above-indentified patent and that said Letters Patent is hereby corrected as shown below:

Column 28, line 28, "[6((4,4-" dhould be --[6-((4,4- --;

Column 29, line 59, "[-((4,4-" should be --[5-((4,4- --.

Column 5, line 40, start a new paragraph with "Some of the compounds ..."

Column 6, line 34, "$R_{25}$*" should be --$R_5$*--;

Column 6, line 40-43, all "$CH_3(CH_2)_2$" should be --$CH_3(CH_2)_3$--;

Column 32, lines 19 and 25, "n is 0" should be --n is 0--.

Signed and Sealed this

First Day of July, 1997

Attest:

BRUCE LEHMAN

*Attesting Officer*  *Commissioner of Patents and Trademarks*